United States Patent [19]

Petrzilka

[11] Patent Number: 5,013,478
[45] Date of Patent: May 7, 1991

[54] LIQUID CRYSTALS

[75] Inventor: Martin Petrzilka, Kaiseraugst, Switzerland

[73] Assignee: Hoffmann-La Roche Inc., Nutley, N.J.

[21] Appl. No.: 239,069

[22] Filed: Aug. 31, 1988

Related U.S. Application Data

[60] Continuation of Ser. No. 925,642, Oct. 31, 1986, abandoned, which is a division of Ser. No. 586,471, Mar. 5, 1984, Pat. No. 4,676,604.

[30] Foreign Application Priority Data

| Mar. 16, 1983 | [CH] | Switzerland | 1436/83 |
| Mar. 22, 1983 | [CH] | Switzerland | 1539/93 |
| Jan. 19, 1984 | [CH] | Switzerland | 226/84 |

[51] Int. Cl.$^5$ .................. C09K 19/30; C09K 19/32; C09K 19/12; G02F 1/13
[52] U.S. Cl. .................. 252/299.63; 252/299.61; 252/299.62; 252/299.65; 252/299.66; 252/299.67; 350/350 R
[58] Field of Search ........... 252/299.6, 299.61, 299.63, 252/299.64, 299.65, 299.66, 299.67; 350/350 R, 350 S

[56] References Cited

U.S. PATENT DOCUMENTS

| 3,819,531 | 6/1874 | Saeva et al. | 252/299.6 |
| 3,939,258 | 7/1983 | Sato et al. | 252/299.61 |

(List continued on next page.)

FOREIGN PATENT DOCUMENTS

| 23730A1 | 6/1981 | European Pat. Off. | 252/299.61 |
| 168683 | 1/1986 | European Pat. Off. | 252/299.63 |
| 2636684 | 2/1978 | Fed. Rep. of Germany | 252/299.63 |
| 3006666 | 5/1981 | Fed. Rep. of Germany | 252/299.63 |
| 2377441 | 8/1978 | France | 252/299.67 |
| 52-13484 | 2/1977 | Japan | 252/299.66 |
| 57-67538 | 4/1982 | Japan | 252/299.63 |
| 57-70851 | 5/1982 | Japan | 252/299.63 |
| 59-199649 | 11/1984 | Japan | 252/299.66 |
| 60-112723 | 6/1985 | Japan | 252/299.63 |
| 60-202830 | 10/1985 | Japan | 252/299.63 |
| 61-24545 | 2/1986 | Japan | 252/299.63 |
| 61-27928 | 2/1986 | Japan | 252/299.63 |
| 61-27929 | 2/1986 | Japan | 252/299.63 |
| 61-27932 | 2/1986 | Japan | 252/299.67 |
| 1432692 | 9/1976 | United Kingdom | 252/299.64 |
| 2002767 | 2/1979 | United Kingdom | 252/299.66 |
| 2078727 | 1/1982 | United Kingdom | 252/299.6 |
| 2092169 | 8/1982 | United Kingdom | 252/299.63 |
| 2137982 | 10/1984 | United Kingdom | 252/299.66 |

OTHER PUBLICATIONS

Schadt., M., et al., Tenth International Liquid Crystal Conf., Abstract G52, York, UK, 15–21 Jul. 1984.
Petrzilka, M., Mol. Cryst. Liq. Cryst., vol. 111, pp. 329–346 (1984).
Hsu, E. G. et al., Mol. Cryst. Liq. Cryst., vol. 33, pp. 35–45 (1976).
Demus, D., et al., Flussige Kristalle in Tabbellen, Veb Deutscher Verlag Fur Grundstoffindustrie, Leipzig, p. 96 (1974).
Kamogawa, H., Bull. Chem. Soc. Japan, vol. 52, No. 10, pp. 3125–3126 (1979).
Mol. Cryst. Liq. Cryst. 63, 129 (1981).
Dabrowski, R., et al., Mol. Cryst. Liq. Cryst., vol. 87, pp. 109–135 (1982).
Mol. Cryst. Liq. Cryst. 95: 255–266 (1983).
Chem.-Ztg. 104: 269 (1980) and its Chem. Abst. 94: 139275c (1981).
Dubois, et al., Nouveau Journal de Chemie 2, 643 (1978).
Mizuno, et al., Mol. Crystl. Liq. Cyst. 41, 161 (1978).
Kamogawa, et al., Bull. Chem. Soc. Japan 56, 3517 (1983).
Chem Abst. 63: 14729h (1965).
Chem Abst. 89: 110437t (1978).
Goodby, et al., Liq. Crystl. Ordered Fluids 4, 89 (1984).

Primary Examiner—Richard D. Lovering
Assistant Examiner—Cynthia Harris
Attorney, Agent, or Firm—George M. Gould; Bernard S. Leon; George W. Johnston

[57] ABSTRACT

Compounds of the formula

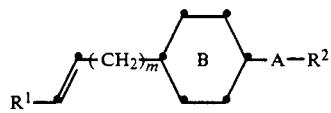

wherein, inter alia, $R^1$ is hydrogen or straight-chain alkyl; $R^2$ is —CN, —R, —COR, —COOR; R is alkyl; A is a group with 1 to 4 six-membered rings, these rings being linked directly with one another and with ring B in each case via a single covalent bond or being linked at one or two positions also via ester or ether groups; the six-membered rings in A and ring B each are 1,4-phenylene or trans-1,4-cyclohexylene or one of these rings also is trans-2,5-disubstituted m-dioxane; m can be 0 when ring B is trans-1,4-cyclohexylene or trans-2,5-disubstituted m-dioxane, liquid crystalline mixtures which contain these compounds as well as their use for electro-optical purposes are described.

27 Claims, No Drawings

U.S. PATENT DOCUMENTS

| | | | |
|---|---|---|---|
| 3,947,375 | 3/1976 | Gray et al. | 252/299.67 |
| 3,997,536 | 12/1976 | Boller et al. | 252/299.61 |
| 4,062,798 | 12/1977 | Boller et al. | 252/299.61 |
| 4,130,502 | 12/1978 | Eidenschink et al. | 252/299.63 |
| 4,147,655 | 4/1979 | Dubois et al. | 252/299.67 |
| 4,154,697 | 5/1979 | Eidenschink et al. | 252/299.63 |
| 4,181,625 | 1/1980 | Eidenschink et al. | 252/299.63 |
| 4,200,580 | 4/1980 | Hsu | 252/299.61 |
| 4,211,666 | 7/1980 | Inukai et al. | 252/299.66 |
| 4,261,651 | 4/1981 | Gray et al. | 252/299.63 |
| 4,273,929 | 6/1981 | Boller et al. | 252/299.61 |
| 4,322,354 | 3/1982 | Sorkin | 252/299.61 |
| 4,325,830 | 4/1982 | Sethofer | 252/299.61 |
| 4,331,552 | 5/1982 | Eidenschink et al. | 252/299.63 |
| 4,348,324 | 9/1982 | Demus et al. | 252/299.61 |
| 4,358,391 | 11/1982 | Finkelmann et al. | 252/299.01 |
| 4,363,767 | 10/1982 | Demus et al. | 252/299.63 |
| 4,388,453 | 6/1983 | Finkelmann et al. | 252/299.67 |
| 4,419,262 | 12/1983 | Petrzilka et al. | 252/299.61 |
| 4,422,951 | 12/1983 | Sugimori et al. | 252/299.63 |
| 4,439,015 | 3/1984 | Rich et al. | 252/299.63 |
| 4,460,770 | 7/1984 | Petrzilka et al. | 252/299.63 |
| 4,486,332 | 12/1984 | Demus et al. | 252/299.61 |
| 4,505,837 | 3/1985 | Romer et al. | 252/299.63 |
| 4,526,704 | 7/1985 | Petrzilka et al. | 252/299.63 |
| 4,528,114 | 7/1985 | Petrzilka et al. | 252/299.63 |
| 4,550,981 | 11/1985 | Petrzilka et al. | 252/299.63 |
| 4,565,425 | 1/1986 | Petrzilka et al. | 252/299.63 |
| 4,572,794 | 2/1986 | Eidenschink et al. | 252/299.63 |
| 4,583,826 | 4/1986 | Petrzilka et al. | 252/299.63 |
| 4,595,521 | 6/1986 | Petrzilka et al. | 252/299.61 |
| 4,621,901 | 11/1986 | Petrzilka et al. | 252/299.63 |
| 4,629,581 | 12/1986 | Boller et al. | 252/299.61 |
| 4,630,896 | 12/1986 | Petrzilka et al. | 252/299.63 |
| 4,654,421 | 3/1987 | Tanaka et al. | 252/299.63 |
| 4,676,604 | 6/1987 | Petrzilka | 252/299.61 |
| 4,704,227 | 11/1987 | Krause et al. | 252/299.61 |
| 4,708,441 | 11/1987 | Petrzilka et al. | 252/299.64 |
| 4,709,030 | 11/1987 | Petrzilka et al. | 252/299.63 |
| 4,719,032 | 1/1988 | Wachtler et al. | 252/299.63 |

LIQUID CRYSTALS

This application is a continuation of application Ser. No. 925,642, filed Oct. 13, 1986 now abandoned, which in turn is a divisional of U.S. application Ser. No. 586,471 filed Mar. 5, 1984, now U.S. Pat. No. 4,676,604.

BACKGROUND OF THE INVENTION

1. Field of the Invention

This invention relates to liquid crystalline compounds and mixtures.

2. Description

Liquid crystals have recently gained considerably importance primarily as dielectrics in indicating devices, since the optical properties of such substances can be influenced by an applied voltage. Electro-optical devices based on liquid crystals are well known to the person skilled in the art and can be based on various effects such as, for example, dynamic scattering, the deformation of aligned phases (DAP type), the Schadt-Helfrich effect (rotation cell), the guest/host effect or a cholestericnematic phase transition (phase change effect).

Liquid crystals must satisfy a number of requirements in order to be suitable as dielectrics for electro-optical indicating devices. For example, they must have a good chemical stability towards environmental factors such as, for example, heat, moisture, air and electromagnetic radiation in the infrared, visible and ultraviolet range. Further, they should be colourless, should have short response times and should have not too high a viscosity, should give a good contrast and should have a nematic or cholesteric mesophase in the entire temperature range in which the liquid crystal cell is to be operated. Other properties must fulfil different conditions depending on the type of cell which is used; for example, liquid crystals which are used in rotation cells should have a large positive anisotropy of the dielectric constants ($\Delta\epsilon = \epsilon_{\parallel} - \epsilon_{\perp} > 0$, $\epsilon_{\parallel}$ signifying the dielectric constant along the longitudinal molecular axis and $\epsilon_{\perp}$ signifying the dielectric constant perpendicular thereto) and liquid crystals which are used in guest/host cells should have a large positive or negative anisotropy of the dielectric constants. Moreover, in both cases a low threshold potential and a conductivity which is as small as possible are desirable.

Since, in general, it is not possible to achieve all desired and to some extent contradictory properties with a single compound, attempts have mainly been made to optimize the properties for the particular applications by mixing several components. In this case it is, however, important that the components undergo no chemical reactions with one another and have a good miscibility. Further, the mixtures formed should have no smectic mesophases, at least at temperatures at which the liquid crystal cell is to be operated.

There are already known a number of liquid crystalline compounds and doping agents for liquid crystal mixtures which have as wing groups, for example, alkyl, alkoxy, alkanoyloxy, alkoxycarbonyl and cyano groups.

SUMMARY OF THE INVENTION

The invention is concerned with liquid crystal compounds of the formula

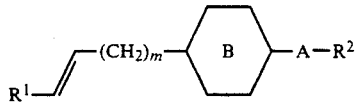

wherein $R^1$ signifies hydrogen or straight-chain alkyl; $R^2$ represents —CN, —R, —COR, —COOR or on an aromatic ring also —OR, —OOCR or fluorine and R denotes alkyl; A stands for a group with 1 to 4 six-membered rings, these rings being linked directly with one another and with ring B in each case via a single covalent bond or being linked at one or optionally two positions also via —COO—, —OOC— or —CH$_2$CH$_2$—; the six-membered rings in A and ring B signify 1,4-phenylene or trans-1,4-cyclohexylene or one of these rings also signifies a trans-2,5-disubstituted m-dioxane ring, a 2,5-disubstituted pyrimidine ring or a 3,6-disubstituted pyridazine ring, and a maximum of two adjacent trans-1,4-cyclohexylene rings are linked directly via a single covalent bond; and m denotes the number 2 or, insofar as ring B signifies trans-1,4-cyclohexylene or a trans-2,5-disubstituted m-dioxane ring, also the number 0.

It has now been found that the above compounds provided by the invention have a satisfactory stability towards electromagnetic radiation and that the trans-1-alkenyl or trans-3-alkenyl side-chain exerts a favourable influence on the mesophase behaviour. Further, the compounds provided by the invention have a good miscibility with known liquid crystals and also have the remaining requisite properties referred to above. Depending on the significance of ring B and of groups A and $R^2$ the compounds provided by the invention cover a broad spectrum of the widest variety of electro-optical applications. For example, the compounds which contain a pyrimidine ring and/or a cyano group have a positive anisotropy of the dielectric constants ($\Delta\epsilon = \epsilon_{\parallel} - \epsilon_{\perp} > 0$, $\epsilon_{\parallel}$ signifying the dielectric constant along the longitudinal molecular axis and $\epsilon_{\perp}$ signifying the dielectric constant perpendicular thereto), while a pyridazine ring confers a negative dielectric anisotropy to the compounds. On the other hand, the compounds which contain no cyano group and no pyrimidine or pyridazine ring have a low viscosity and a small absolute sum of the dielectric anisotropies. The compounds which contain a m-dioxane ring are primarily of interest for producing low threshold potentials and short response times. The compounds provided by the invention are for the most part themselves liquid crystalline and some of them have a very large mesophase range. Those compounds provided by the invention which have only monotropic or virtual clearing points such as, for example, the compounds of formula I in which A signifies 1,4-phenylene or a 3,6-disubstituted pyridazine ring, ring B signifies trans-1,4-cyclohexylene and $R^2$ signifies alkyl or alkoxy are primarily suitable as doping agents for liquid crystal mixtures. The present invention therefore extends considerably the choice of suitable liquid crystal components which, in particular, facilitates the further optimization of mixtures.

The invention is also concerned with the manufacture of the compounds of formula I above, liquid crystalline mixtures which contain compounds of formula I above as well as the use of compounds of formula I above for electro-optical purposes.

The invention is also concerned with liquid crystal compounds of the formula

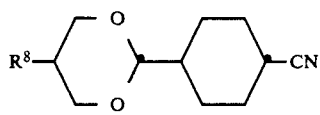

LXXVIII wherein $R^8$ is straight-chain $C_1$–$C_{12}$-alkyl,
as well as the manufacture of the compounds of formula LXXVIII above, liquid crystalline mixtures which contain these compounds and their use for electro-optical purposes.

The compounds of formula LXXVIII have at the same time a large positive anisotropy of the dielectric constants, a small optical anisotropy, low viscosity (especially when used in mixtures), low threshold potentials and short response times as well as an improved mesophase behaviour. Further, they have a high chemical stability and only slight conductivity, they are colourless and have a good miscibility with all customary liquid crystals and give a high contrast in indicating devices. The compounds provided by the invention are therefore very well suited for liquid crystalline dielectrics in electro-optical indicating devices such as, for example, in rotation cells and guest/host cells, especially in rotation cells.

DETAILED DESCRIPTION OF THE INVENTION

As used herein the terms "alkyl" and "$C_1$–$C_{12}$ alkyl" denote straight-chain alkyl groups of 1 to 12 carbon atoms (e.g., methyl, ethyl, propyl, butyl, pentyl, hexyl, heptyl, octyl, nonyl, decyl, undecyl, dodecyl and the like) as well as branched-chain alkyl groups of 1 to 12 carbon atoms, especially 1-methylalkyl and 2-methylalkyl (e.g., isopropyl, isobutyl, sec.butyl, 1-methylbutyl, 2-methylbutyl, 1-methylpentyl, 2-methylpentyl, 1-methylhexyl, 2-methylhexyl and the like).

The terms "straight-chain alkyl" and "$C_1$–$C_{12}$ straight-chain alkyl" denote straight-chain alkyl groups of 1 to 12 carbon atoms.

The terms "alkoxy" and "alkoxycarbonyl", as well as any other groups in the specification containing "alkyl", denotes moieties in which their "alkyl" portions are as defined previously.

The term "alkanoyloxy" denotes moieties derived from alkanecarboxylic acid moieties of 2 to 13 carbon atoms.

The term "halogen" denotes chlorine, bromine or iodine.

Ring B is 1,4-phenylene, trans-1,4-cyclohexylene, a trans-2,5-disubstituted m-dioxane ring, a 2,5-disubstituted pyrimidine ring or a 3,6-disubstituted pyridazine ring. Group A contains 1 to 4 six-membered rings. The rings in group A can signify 1,4-phenylene and/or trans-1,4-cyclohexylene. When ring B stands for 1,4-phenylene or trans-1,4-cyclohexylene, one of the rings in group A can also signify a trans-2,5-disubstituted m-dioxane ring, a 2,5-disubstituted pyrimidine ring or a 3,6-disubstituted pyridazine ring. Each trans-1,4-cyclohexylene ring which may be present in formula I can be linked directly with at most one further trans-1,4-cyclohexylene ring via a single covalent bond.

The term "aromatic ring" used herein denotes a benzene, pyrimidine or pyridazine ring. The term "heterocyclic ring" denotes in the scope of the present invention a pyrimidine, pyridazine or m-dioxane ring.

The invention is concerned with novel liquid crystal components containing a trans-1-alkenyl or a trans-3-alkenyl side-chain, namely compounds of the general formula

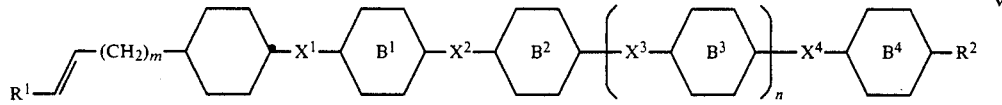

I wherein $R^1$ is hydrogen or straight-chain alkyl; $R^2$ is —CN, —R, —COR, —COOR or when $R^2$ is positioned on an aromatic ring $R^2$ also can be —OR, —OOCR or —F; R is alkyl; A is a group with 1 to 4 six-membered rings, these rings being linked directly with one another and with ring B in each case via a single covalent bond or being linked at one or two positions also via —COO—, —OOC— or —CH$_2$CH$_2$—; the six-membered rings in A and ring B each are 1,4-phenylene or trans-1,4-cyclohexylene or one of these rings also is trans-2,5-disubstituted m-dioxane, 2,5-disubstituted pyrimidine or 3,6-disubstituted pyridazine, with the proviso that a maximum of two adjacent trans-1,4-cyclohexylene rings are linked directly via a single covalent bond; and m is the integer 2, or when ring B is trans-1,4-cyclohexylene or trans-2,5-disubstituted m-dioxane, m also can be the integer 0.

A preferred group of compounds within formula I having the formula

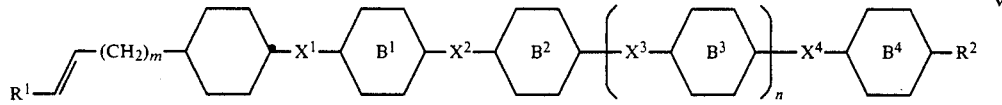

V wherein each of rings $B^1$, $B^2$, $B^3$ and $B^4$ is 1,4-phenylene or trans-1,4-cyclohexylene; n is the integer 0 or 1; each of $X^1$, $X^2$, $X^3$ and $X^4$ is a single covalent bond or one or two of these symbols also is —COO—, —OOC— or —CH$_2$CH$_2$—, with the proviso that a maximum of two adjacent trans-1,4-cyclohexylene rings are linked directly via a single covalent bond; and $R^1$, $R^2$, R and m have the significances given above.

Preferably, m in formula V stands for the number 0. Especially preferred compounds of formula V are those in which $X^1$ denotes a single covalent bond, —COO— or —CH$_2$CH$_2$—, the symbols $X^2$, $X^3$ and $X^4$ represent single covalent bonds, the rings $B^1$, $B^2$ and $B^3$ stand for 1,4-phenylene and $R^2$ signifies cyano, alkyl or on an aromatic ring also alkoxy. Further, ring $B^4$ preferably stands for trans-1,4-cyclohexylene when $R^2$ signifies alkyl and ring $B^4$ preferably stands for 1,4-phenylene when $R^2$ signifies cyano.

However, in general, the bicyclic and the tricyclic compounds, (i.e. the compounds of formula I in which group A has one or two six-membered rings,) stand in the foreground of interest. Preferred compounds provided by the invention are therefore the compounds of the formula

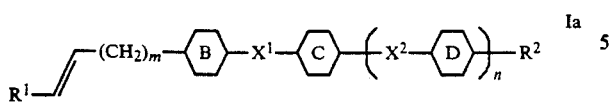

wherein rings B, C and D each are 1,4-phenylene, trans-1,4-cyclohexylene or one of these rings also can be trans-2,5-disubstituted m-dioxane, 2,5-disubstituted pyrimidine or 3,6-disubstituted pyridazine; one of $X^1$ and $X^2$ is a single covalent bond and the other is —COO—, —OOC—, —CH$_2$CH$_2$—, or when at least one of the rings B, C and D is not trans-1,4-cyclohexylene, the other of $X^1$ and $X^2$ also can be a single covalent bond; n is the integer 0 or 1; and $R^1$, $R^2$, R and m have the significances given above.

Ring B in formulae I and Ia preferably stands for trans-1,4-cyclohexylene or a trans-2,5-disubstituted m-dioxane ring. Further, in formula Ia n preferably stands for the number 0. In general, m preferably stands for the number 0 when ring B signifies trans-1,4-cyclohexylene or a trans-2,5-disubstituted m-dioxane ring.

Preferred compounds falling under formulae I and Ia are the compounds of the formula

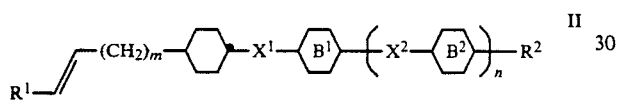

wherein each of rings $B^1$ and $B^2$ is 1,4-phenylene or trans-1,4-cyclohexylene; one of $X^1$ and $X^2$ is a single covalent bond and the other is —COO—, —OOC—, —CH$_2$CH$_2$—, or when at least one of the rings $B^1$ and $B^2$ is not trans-1,4-cyclohexylene, the other of $X^1$ and $X^2$ also can be a single covalent bond; n is the integer 0 or 1; and $R^1$, $R^2$, R and m have the significances given above, the compounds of the formula

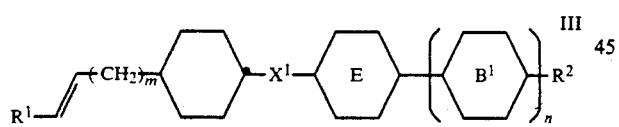

wherein ring E is 2,5-disubstituted pyrimidine; ring $B^1$ is 1,4-phenylene or trans-1,4-cyclohexylene; $X^1$ is a single covalent bond, —COO—, —OOC— or —CH$_2$CH$_2$—; n is the integer 0 or 1; and $R^1$, $R^2$, R and m have the significances given above, the compounds of the formula

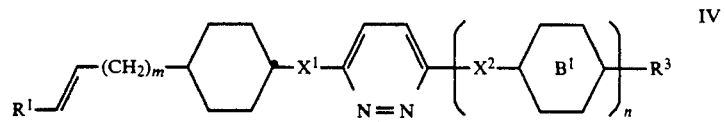

wherein ring $B^1$ is 1,4-phenylene or trans-1,4-cyclohexylene; each of $X^1$ and $X^2$ is a single covalent bond or one of $X^1$ and $X^2$ also is —COO—, —OOC— or —CH$_2$CH$_2$—; n is the integer 0 or 1; $R^3$ is —R, —COR, —COOR, or when $R^3$ is positioned on an aromatic ring $R^3$ also can be —OR or —OOCR; and $R^1$, R and m have the significances given above, and the compounds of the formula

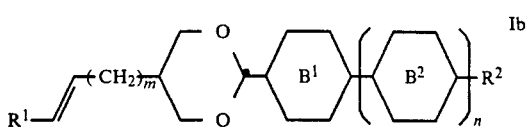

wherein each of rings $B^1$ and $B^2$ is 1,4-phenylene or trans-1,4-cyclohexylene; n is the integer 0 or 1; and $R^1$, $R^2$, R and m have the significances given above.

Especially preferred compounds of formula II are those in which $X^1$ denotes a single covalent bond, —COO—, —OOC— or —CH$_2$CH$_2$— and $X^2$ denotes a single covalent bond, rings $B^1$ and $B^2$ represent 1,4-phenylene and $R^2$ signifies cyano, alkyl or alkoxy. Further, in formula II n preferably signifies the number 0 and/or $X^1$ preferably signifies a single covalent bond.

Especially preferred compounds of formula III are those in which $X^1$ is present in the 5-position of the pyrimidine ring E and denotes a single covalent bond. Preferred groups denoted by $R^2$ are alkyl, alkoxy and especially cyano. Preferably, n stands for the number 1 and ring $B^1$ stands for 1,4-phenylene.

Especially preferred compounds of formula IV are those in which $X^1$ and $X^2$ denote single covalent bonds or one of these symbols also denotes —CH$_2$CH$_2$— and $R^3$ signifies alkyl or on an aromatic ring also alkoxy, particularly those compounds in which $X^1$ denotes a single covalent bond and n denotes the number 0.

Especially preferred compounds of formula Ib are those in which n denotes the number 0 and $R^2$ denotes cyano, alkyl or on an aromatic ring also alkoxy. Ring $B^1$ preferably stands for 1,4-phenylene.

The group R in the above definitions of $R^2$ and $R^3$ is conveniently an alkyl group containing 1 to 12 carbon atoms, especially a straight-chain alkyl group containing 1 to 12 carbon atoms.

Further, there are, in principle, preferred those compounds of formula I in which $R^2$ signifies cyano, alkyl or on an aromatic ring also alkoxy. Preferred alkyl and alkanoyl groups $R^2$ or $R^3$ are those containing 3 to 7 carbon atoms and preferred alkoxy, alkanoyloxy and alkoxycarbonyl groups $R^2$ or $R^3$ are those containing 2 to 6 carbon atoms.

The symbol $R^1$ in formulae I, Ia, Ib, II, III, IV and V above preferably signifies hydrogen or straight-chain $C_1$-$C_{10}$-alkyl, especially hydrogen or straight-chain $C_1$-$C_5$-alkyl, when m stands for the number 0, and preferably signifies hydrogen or straight-chain $C_1$-$C_8$-alkyl, especially hydrogen or straight-chain $C_1$-$C_3$-alkyl, when m stands for the number 2. In the scope of the present invention the term "trans-1-alkenyl" therefore embraces in particular the groups vinyl, trans-1-propenyl, trans-1-butenyl, trans-1-pentenyl, trans-1-hexenyl, trans-1-heptenyl, trans-1-octenyl, trans-1-nonenyl, trans-1-decenyl, trans-1-undecenyl and trans-1-dodecenyl and the term "trans-3-alkenyl" embraces in particular the groups 3-butenyl, trans-3-pentanyl, trans-3-hexenyl, trans-3-heptenyl, trans-3-octenyl, trans-3-nonenyl, trans-3-decenyl, trans-3-undecenyl and trans-3-dodecenyl.

Further preferred groups of compounds provided by the invention and examples of preferred compounds are the compounds falling under formula I which are mentioned in the Reaction Schemes and the Examples hereinafter.

The compounds of formula I can be manufactured in accordance with the invention by the following procedure:

(a) for the manufacture of the compounds of formula I in which $R^1$ signifies primary alkyl containing at least 2 carbon atoms, $R^2$ represents —CN, —R or on an aromatic ring also —OR or fluorine and the rings present in A are linked directly with one another and with ring B in each case via a single covalent bond or are linked at one or optionally two positions also via —CH$_2$CH$_2$—, reacting a compound of the formula

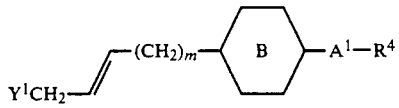
VI wherein $Y^1$ denotes a leaving group; $R^4$ represents —CN, —R or on an aromatic ring also —OR or fluorine and R signifies alkyl; $A^1$ stands for a group with 1 to 4 six-membered rings, these rings being linked directly with one another and with ring B in each case via a single covalent bond or being linked at one or optionally two positions also via —CH$_2$CH$_2$—; the six-membered rings in A and ring B signify 1,4-phenylene or trans-1,4-cyclohexylene or one of these rings also signifies a trans-2,5-disubstituted m-dioxane ring, a 2,5-disubstituted pyrimidine ring or a 3,6-disubstituted pyridazine ring, and a maximum of two adjacent trans-1,4-cyclohexylene rings are linked directly via a single covalent bond; and m denotes the number 2 or, insofar as ring B signifies trans-1,4-cyclohexylene or a trans-2,5-disubstituted m-dioxane ring, also the number 0, with an alkylmagnesium halide in the presence of dilithium tetrachlorocuprate or dilithium tetrabromocuprate, or (b) for the manufacture of the compounds of formula I in which $R^1$ signifies methyl, $R^2$ represents —CN, —R or on an aromatic ring also —OR or fluorine and the rings present in A are linked directly with one another and with ring B in each case via a single covalent bond or are linked at one or optionally two positions also via —CH$_2$CH$_2$—, reducing a compound of formula VI, or (c) for the manufacture of the compounds of formula I in which $R^2$ represents —COR and the rings present in A are linked directly with one another and with ring B in each case via a single covalent bond or are linked at one or optionally two positions also via —CH$_2$CH$_2$—, reacting a compound of the formula

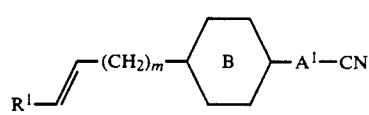
VII wherein $R^1$ denotes hydrogen or straight-chain alkyl and $A^1$, m and ring B have the significances given in formula VI, with an alkylmagnesium halide in the presence of dilithium tetrachlorocuprate or dilithium tetrabromocuprate, or (d) for the manufacture of the compounds of formula I in which A contains at least one group —COO— or —OOC— and/or $R^2$ represents —COOR or —OOCR, esterifying a compound of the formula

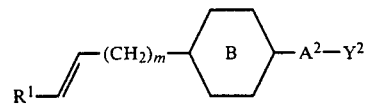
VIII with a compound of the formula $$Y^3-A^3-R^5 \qquad \text{IX}$$

wherein $R^1$ signifies hydrogen or straight-chain alkyl; one of the symbols $Y^2$ and $Y^3$ represents —COOH or —COCl and the other represents —OH; $A^2$ and $A^3$ each stand for a group with 1 to 4 six-membered rings or one of the groups $A^2$ and $A^3$ can also be absent, with the proviso that $A^2$ and $A^3$ together contain a maximum of 4 rings; ring B is linked directly via a single covalent bond optionally with six-membered rings present in $A^2$ and, insofar as $A^2$ and/or $A^3$ have several six-membered rings, these rings are linked directly with one another in each case via a single covalent bond or one or, insofar as $A^3$ is absent, optionally also two of these linkages are effected via —COO—, —OOC— or —CH$_2$CH$_2$—; the six-membered rings in $A^2$ and $A^3$ and ring B signify 1,4-phenylene or trans-1,4-cyclohexylene or one of these rings also signifies a trans-2,5-disubstituted m-dioxane ring, a 2,5-disubstituted pyrimidine ring or a 3,6-disubstituted pyridazine ring, and a maximum of two adjacent trans-1,4-cyclohexylene rings are linked directly via a single covalent bond; m denotes the number 2 or, insofar as ring B signifies trans-1,4-cyclohexylene or a trans-2,5-disubstituted m-dioxane ring, also the number 0; and $R^5$ represents —CN, —R, —COR, —COOR or on an aromatic ring also —OR, —OOCR or fluorine when $A^3$ stands for a group with 1 to 4 six-membered rings or $R^5$ represents —R when $A^3$ is absent and R denotes alkyl, or (e) for the manufacture of the compounds of formula I in which $R^2$ represents —CN, —R or on an aromatic ring also —OR or fluorine and the rings present in A are linked directly with one another and with ring B in each case via a single covalent bond or are linked at one or optionally two positions also via —CH$_2$CH$_2$—, reacting a compound of the formula

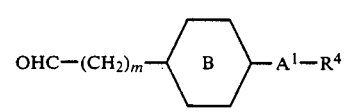
X wherein $A^1$, $R^4$, m and ring B have the significances given in formula VI, with an alkyltriphenylphosphonium halide in the presence of a base, or (f) for the manufacture of the compounds of formula I in which ring B or one of the six-membered rings in A signifies a trans-2,5-disubstituted m-dioxane ring, reacting a compound of the formula

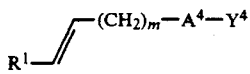  XXXV with a compound of the formula

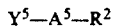  XXXVI wherein $R^1$ signifies hydrogen or straight-chain alkyl; $R^2$ represents —CN, —R, —COR, —COOR or on an aromatic ring also —OR, —OOCR or fluorine and R denotes alkyl; one of the symbols $Y^4$ and $Y^5$ signifies —CH(CH$_2$OH)$_2$ and the other signifies —CHO or an acetal group; $A^4$ and $A^5$ each stand for a group with 1 to 4 1,4-phenylene or trans-1,4-cyclohexylene rings or one of the groups $A^4$ and $A^5$ can also be absent, with the proviso that $A^4$ and $A^5$ together contain a maximum of 4 rings; $Y^4$ and $Y^5$ are linked directly via a single covalent bond optionally with six-membered rings present in $A^4$ or in $A^5$ and, insofar as $A^4$ and/or $A^5$ have several six-membered rings, these rings are linked directly with one another in each case via a single covalent bond or one or two of these linkages are effected via —COO—, —OOC— or —CH$_2$CH$_2$—; a maximum of two adjacent trans-1,4-cyclohexylene rings are linked directly via a single covalent bond; and m signifies the number 2 or, when $A^4$ is absent or the group $R^1$—CH=CH—(CH$_2$)$_m$— stands on a trans-1,4-cyclohexylene ring, also the number 0.

The reaction of a compound of formula VI with an alkylmagnesium halide (process variant a) can be carried out in a manner known per se. The term "halide" used in this connection stands for chloride, bromide or iodide, preferably for bromide. Dilithium tetrachlorocuprate is the preferred catalyst. $Y^1$ signifies any leaving group which is usual in such reactions, for example alkanoyloxy, alkylsulphonyloxy, arylsulphonyloxy or halogen such as acetoxy, methanesulphonyloxy, benzenesulphonyloxy, tosyloxy, naphthalenesulphonyloxy, bromine, iodine and the like. The reaction is conveniently carried out in an ether such as dimethoxyethane, diethylene glycol dimethyl ether, tetrahydrofuran, dioxan, diethyl ether and the like. The solvent is preferably tetrahydrofuran or a mixture of tetrahydrofuran and diethyl ether. The temperature and pressure can be held in wide limits. However, the reaction is generally carried out at atmospheric pressure and at a temperature between about −80° C. and room temperature. The reaction is preferably carried out at a temperature of below about 0° C. and especially at about −15° C.

The reduction of a compound of formula VI in accordance with process variant (b) can be carried out according to methods known per se; for example, by reacting a compound of formula VI in which $Y^1$ signifies iodine with triphenylphosphonium iodide and by reacting a compound of formula VI in which $Y^1$ signifies acetoxy with methanolic potassium hydroxide solution and triphenylphosphine-iodine. Such reactions are described, for example, in Chem. Ber. 109, 1586 (1976).

The reaction of a compound of formula VII with an alkylmagnesium halide (process variant c) can be carried out in an analogous manner to process variant (a). However, it is generally carried out at a somewhat higher temperature, preferably at about 0° C. to the reflux temperature of the reaction mixture.

The esterification of a compound of formula VIII with a compound of formula IX (process variant d) can be carried out in a manner known per se. The esterification of the acid chlorides (which can be obtained from the carboxylic acids, for example by heating with thionyl chloride) can be carried out, for example, in diethyl ether, tetrahydrofuran, dimethylformamide, benzene, toluene, carbon tetrachloride, pyridine and the like. The esterification of a carboxylic acid is preferably carried out in the presence of 4-(dimethylamino)pyridine and N,N′-dicyclohexylcarbodiimide or in the presence of oxalyl chloride and dimethylformamide. The temperature and pressure at which these esterifications are carried out are not critical and there are generally used atmospheric pressure and a temperature between about −30° C. and the boiling point of the reaction mixture.

The reaction of a compound of formula X with an alkyltriphenylphosphonium halide in the presence of a base (e.g. potassium carbonate) (process variant e) can also be carried out in a manner known per se. The term "halide" used in this connection stands for chloride, bromide or iodide, preferably for bromide. The reaction is conveniently carried out in an inert organic solvent, for example an ether such as diethyl ether, tetrahydrofuran, dioxan and the like. The temperature and pressure are not critical, although the reaction is generally carried out at atmospheric pressure and at a temperature of room temperature up to the reflux temperature of the reaction mixture.

The reaction of a compound of formula XXXV with a compound of formula XXXVI (process variant f) can be carried out in a manner known per se. The reaction of the diol with the aldehyde or a suitable acetal thereof (e.g. the dimethyl acetal) is conveniently carried out in an inert organic solvent in the presence of a catalytic amount of an organic or inorganic acid. Hydrocarbons, especially aromatic hydrocarbons such as benzene, toluene, xylene and the like, are preferred solvents. Dry halogen chloride and sulphonic acids, especially p-toluenesulphonic acid, are preferred acids. The temperature and pressure are not critical, but the reaction is preferably carried out at the reflux temperature of the reaction mixture and under atmospheric pressure. The dioxanes are generally obtained as cis/trans mixtures, from which the pure trans compounds can be obtained readily by recrystallization. If desired, the mother liquors can be converted with acid into the cis/trans equilibrium mixture which can again be subjected to recrystallization.

In the manufacture of compounds of formula I in which m signifies the number 0 and ring B signifies trans-1,4-cyclohexylene according to process variant (e) the cyclohexane ring is obtained almost exclusively (about 98%) in the trans-configuration; this also applies when a cis/trans isomer mixture (a compound of formula X in which m signifies the number 0 and ring B signifies cis-1,4-cyclohexylene or trans-1,4-cyclohexylene) is used as the starting material. This process therefore also provides an excellent possibility for the manufacture of corresponding trans-4-alkylcyclohexyl compounds by subsequent catalytic hydrogenation in a manner known per se (e.g. with palladium, platinum or Raney-nickel).

The compounds of formulae IX and XXXVI are known or can be prepared from known compounds by conventional techniques.

The compounds of formulae VI, VIII, X and XXXV are novel and are likewise objects of the present invention. The manufacture of the compounds of formula I and the preparation of the compounds of formulae VI, VII, VIII, X and XXXV is illustrated on the basis of representative examples in Reaction Schemes 1–11 hereinafter in which $R^6$ denotes straight-chain alkyl, $R^7$ denotes hydrogen or straight-chain alkyl, Ts denotes p-tosyl and ring $B^1$ denotes 1,4-phenylene or trans-1,4-cyclohexylene and $R^1$, $R^4$ and R have the above significances. The starting materials which are required in these Reaction Schemes are known or are analogues of known compounds.

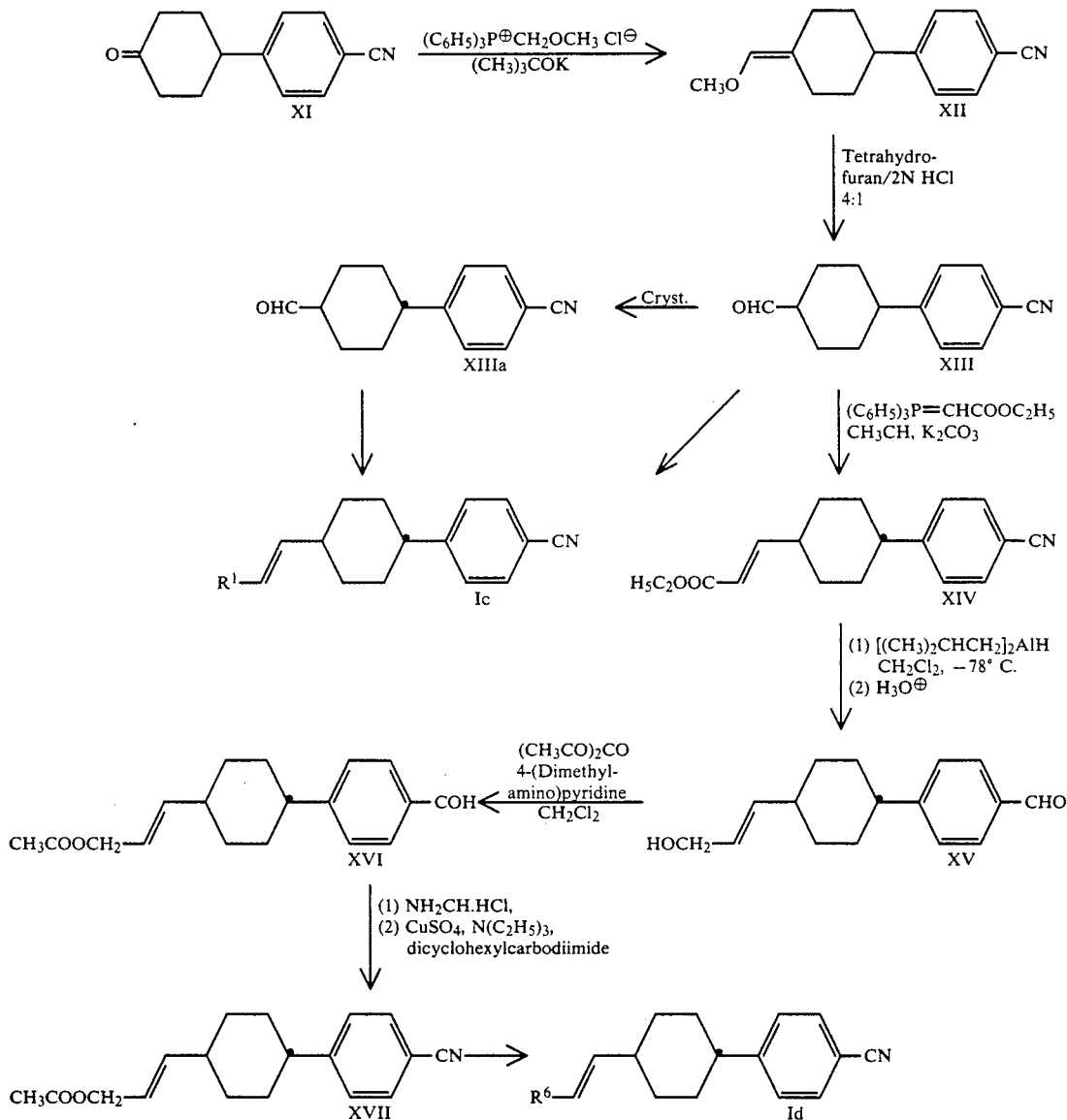

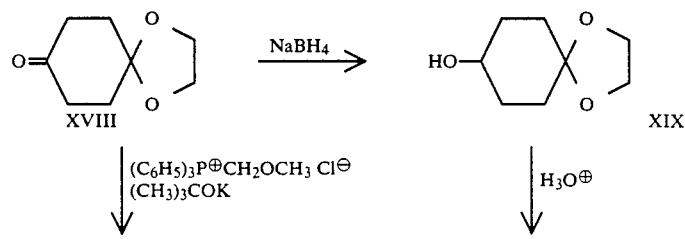

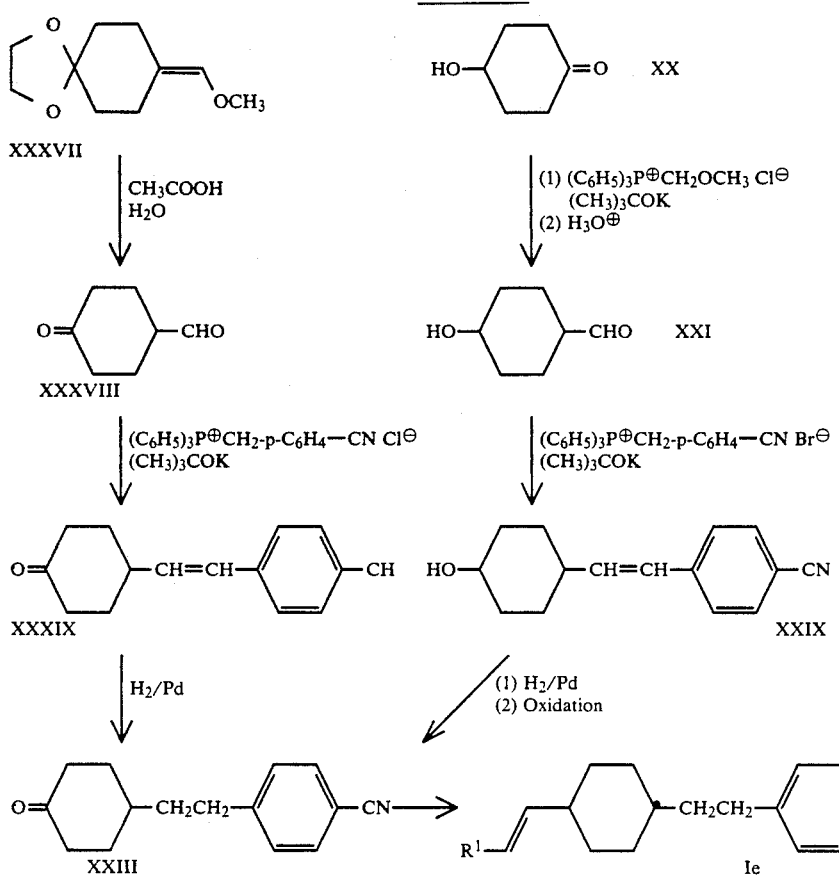
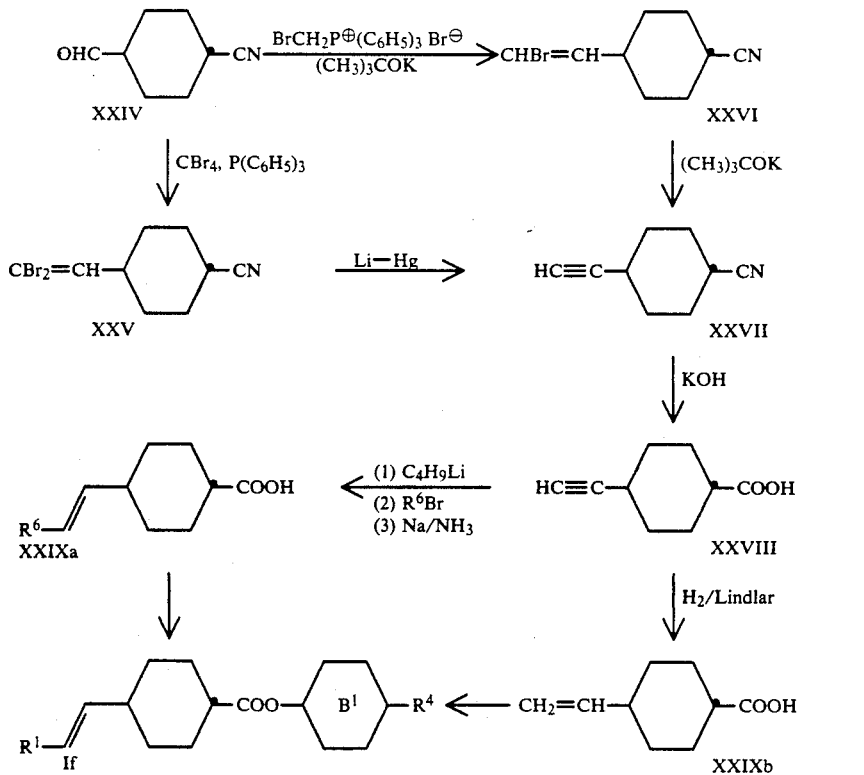

Scheme 4
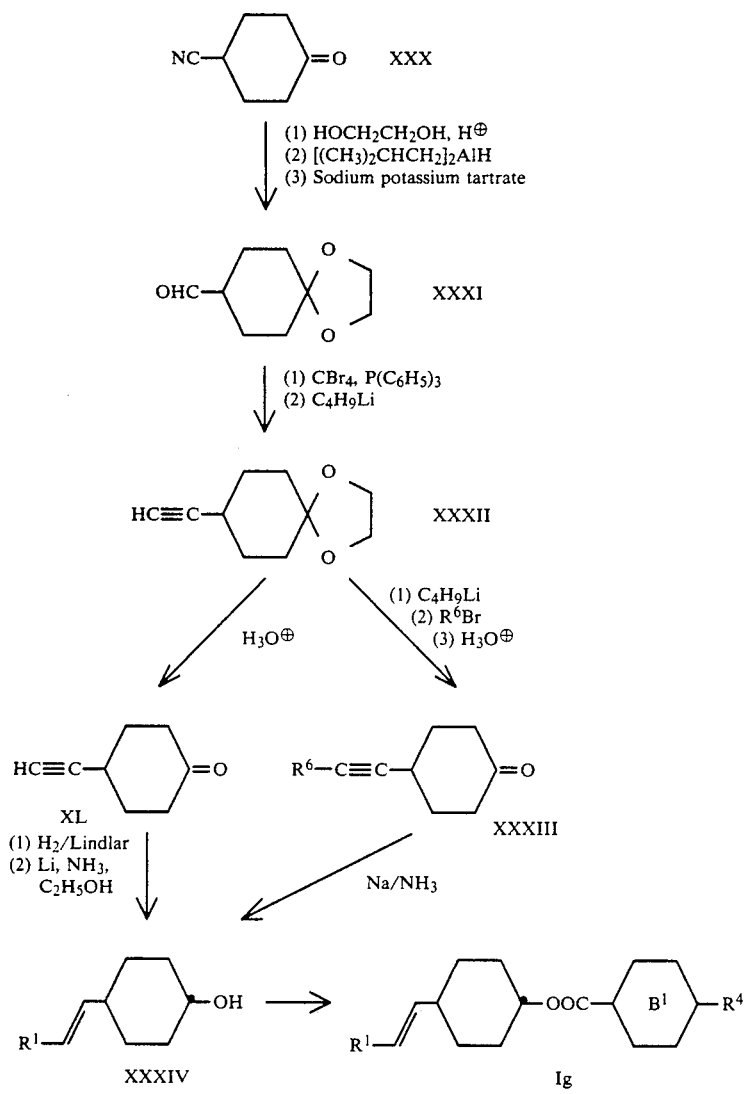
Scheme 5
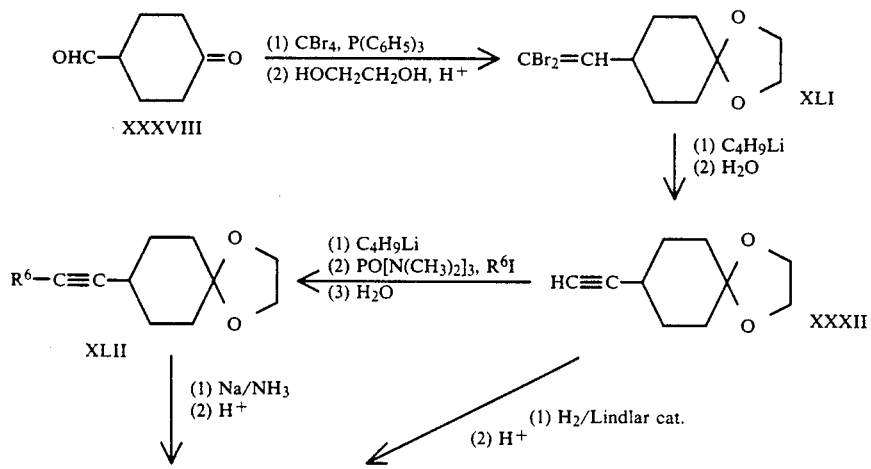

-continued
Scheme 5
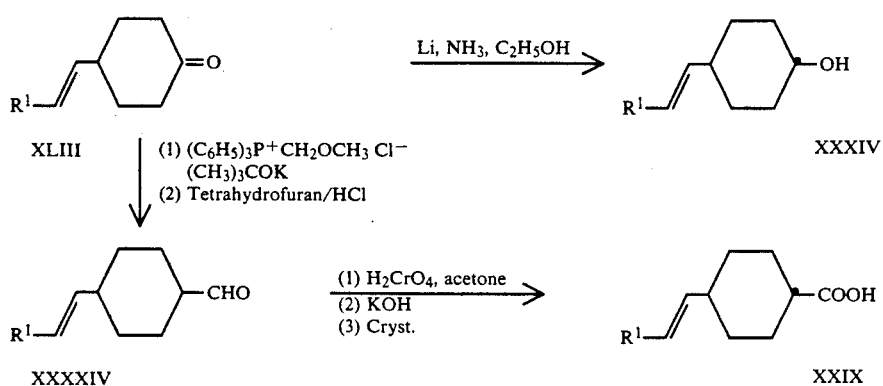
Scheme 6
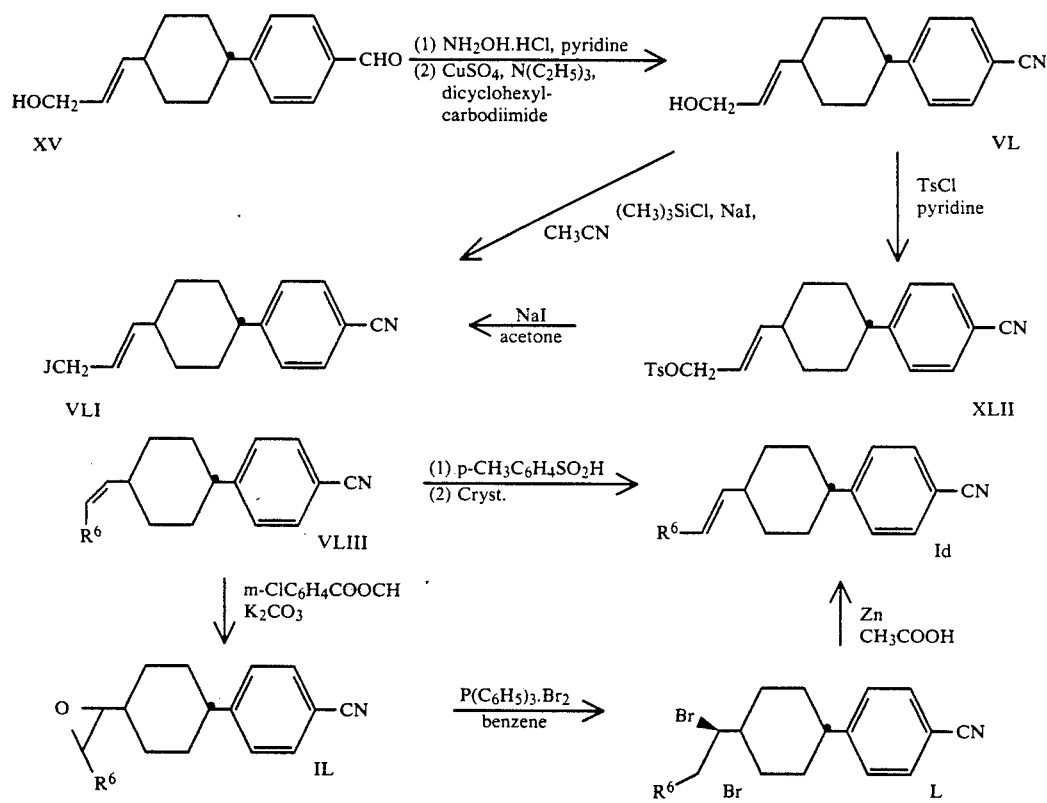
Scheme 7
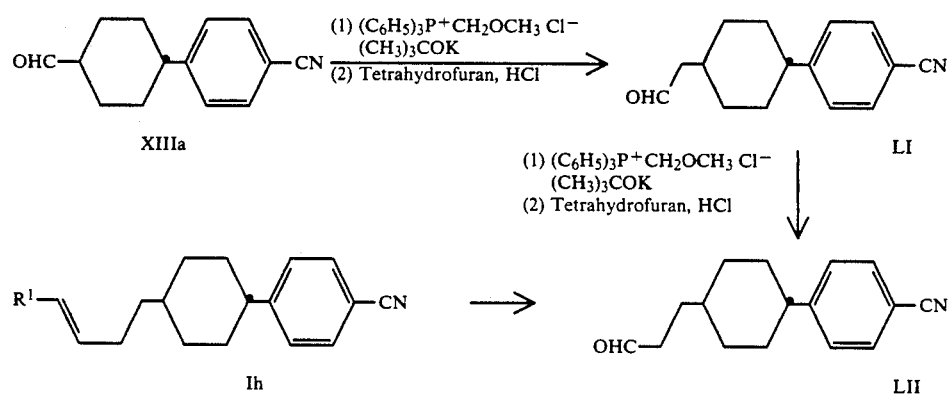

Scheme 7
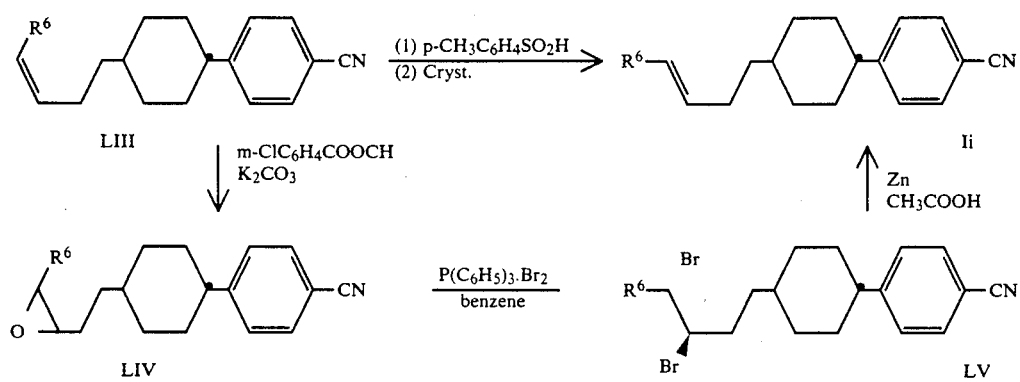
Scheme 8
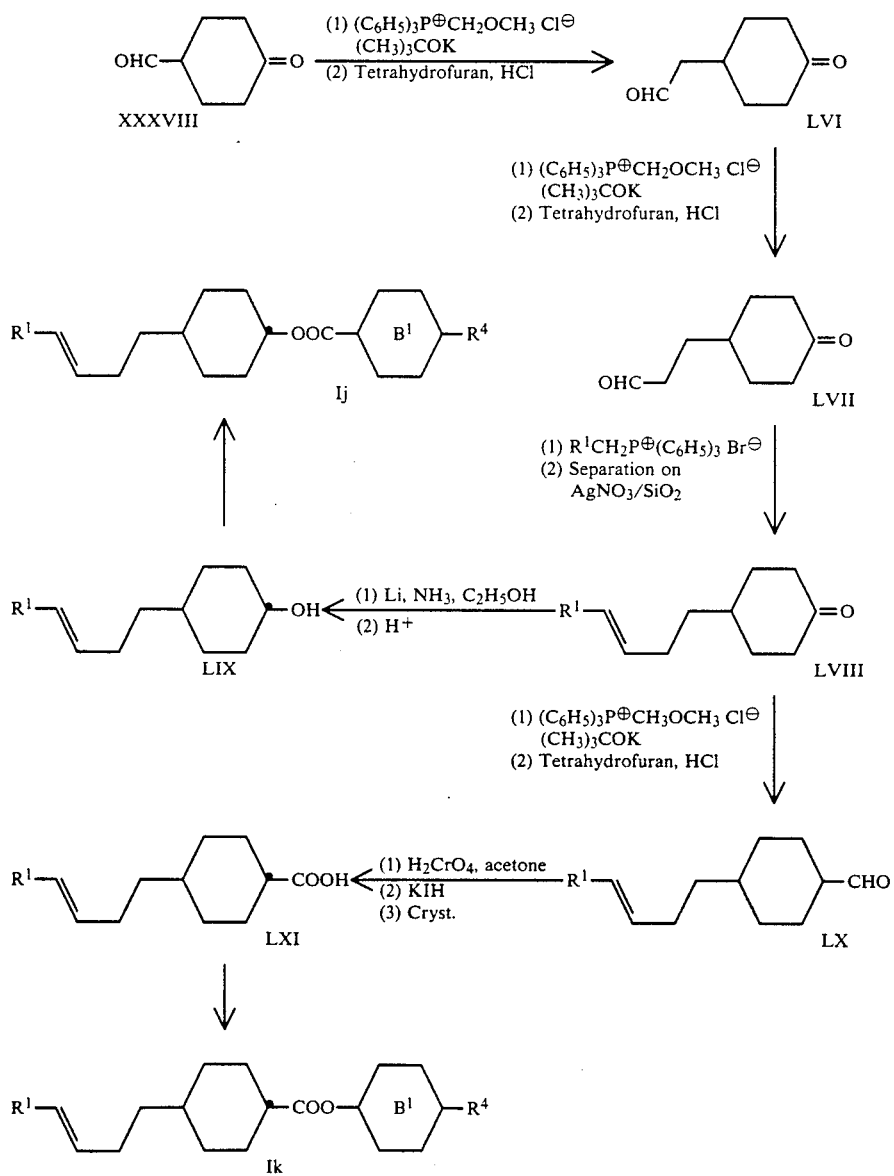

Scheme 9
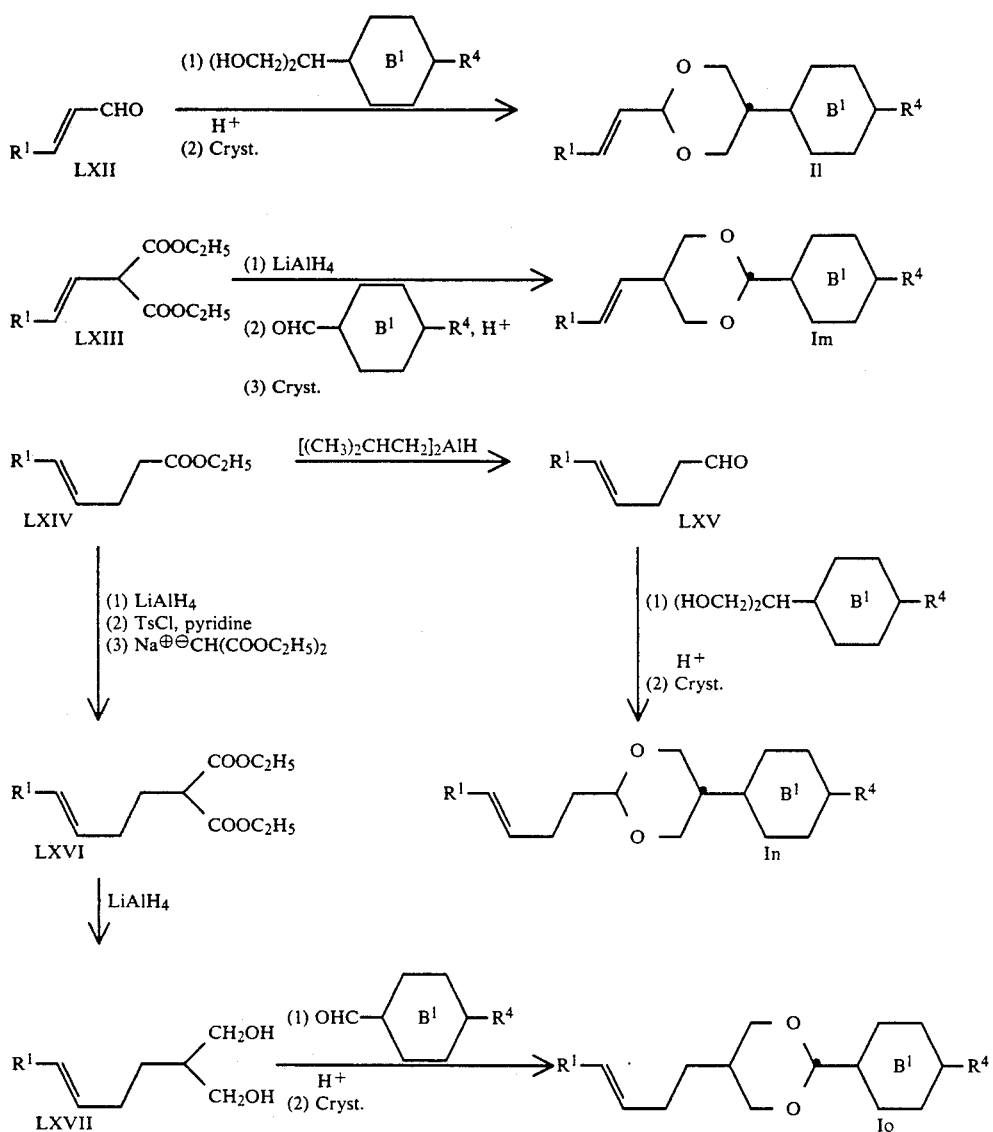
Scheme 10
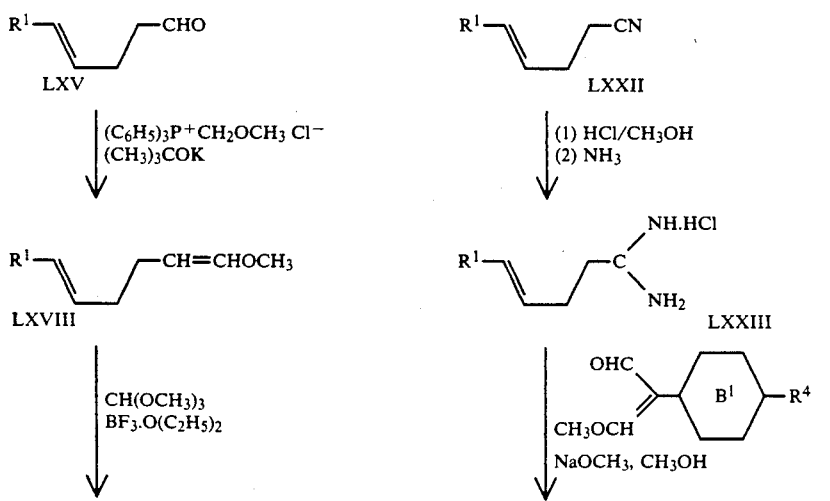

-continued
Scheme 10
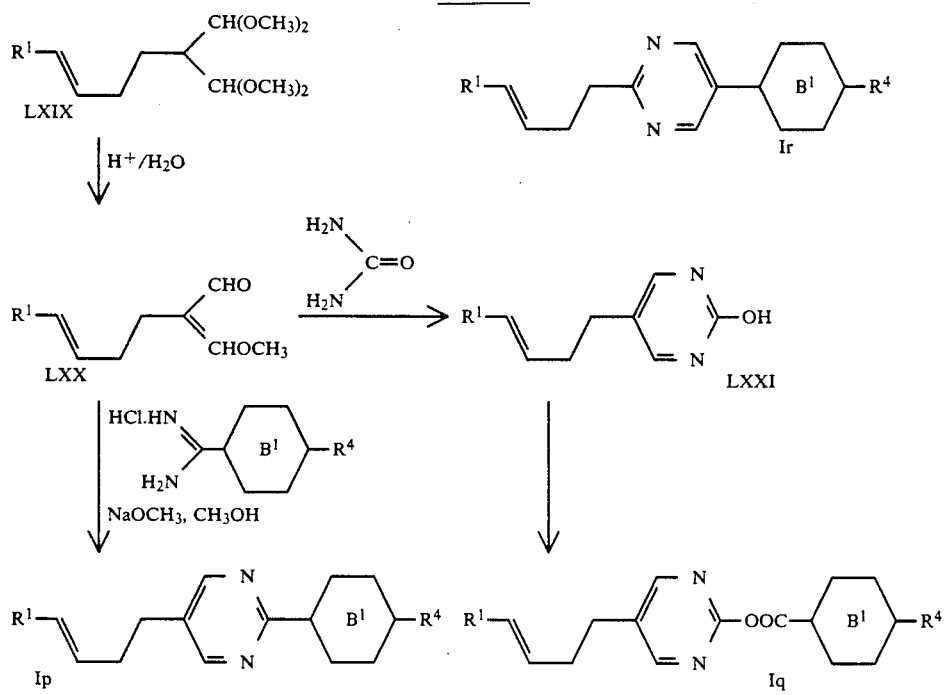
Scheme 11
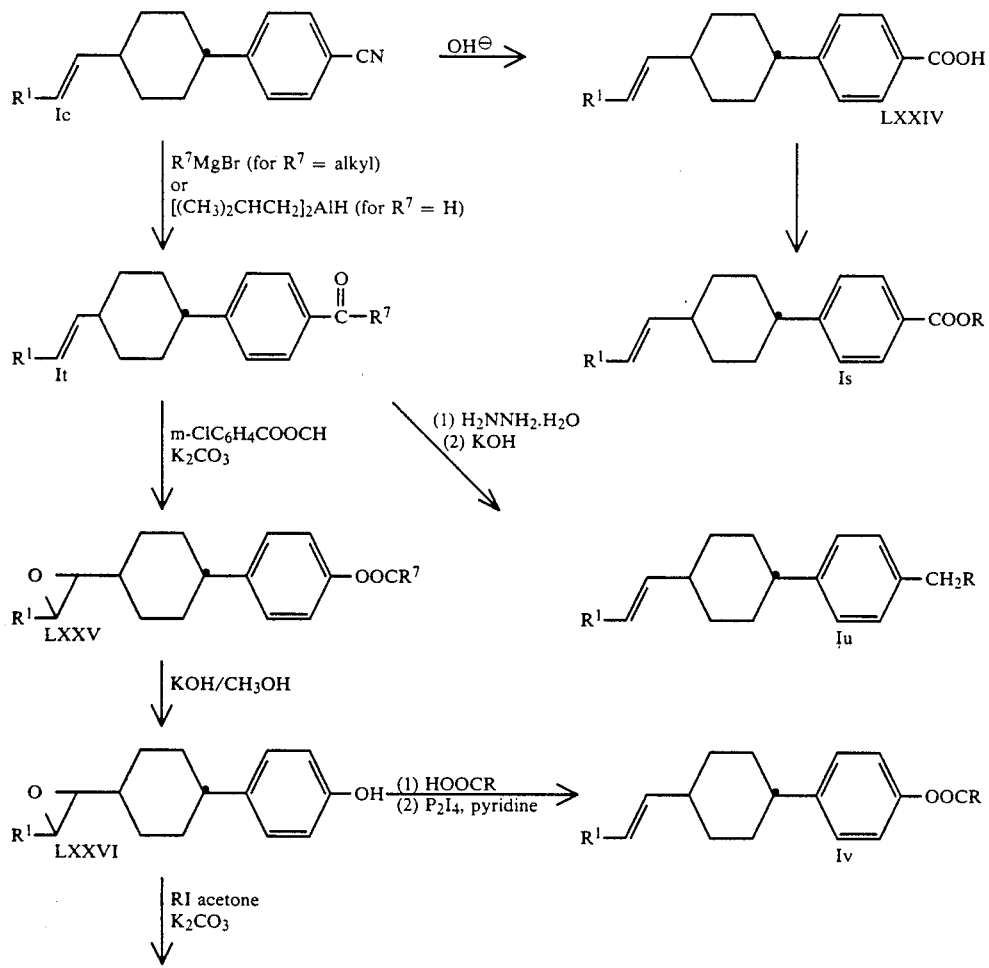

-continued
Scheme 11

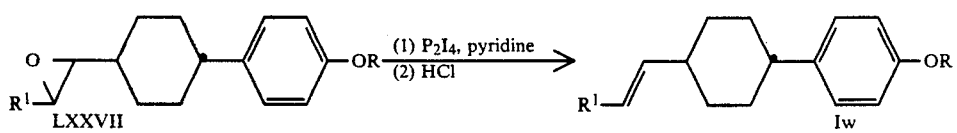

If in place of the cyano compound of formula XI there is reacted in accordance with Scheme 1 a corresponding alkyl, alkoxy or fluoro compound, then the penultimate step (XVI→XVII) can be omitted, since alkyl, alkoxy and fluorine are not affected in the reduction with diisobutylaluminium hydride. The introduction of other leaving groups $Y^1$ (in place of the acetoxy group in formula XVII or analogous compounds) can be carried out according to methods known per se. Further examples are given in Scheme 6.

In the manufacture of the compounds of formulae Ic and Ih in which $R^1$ signifies straight-chain alkyl in accordance with Scheme 1 or 7 (process variant e) there generally results a mixture consisting of cis-alkenyl compound and trans-alkenyl compound. Such mixtures can be separated by chromatography on silica gel coated with silver nitrate. If desired, the cis-alkenyl compounds (or mixtures containing predominantly cis-alkenyl compound) can be converted into the corresponding trans-alkenyl compounds in accordance with Scheme 6 or 7.

The reaction XXIII→Ie in accordance with Scheme 2 can be carried out in an analogous manner to Scheme 1.

The preparation of acids and alcohols of formula VIII and the introduction of trans-3-alkenyl groups are illustrated in Schemes 3–5, 7 and 8. Additional acids of formula VIII can also be obtained by saponifying nitriles of formula VII.

The manufacture of compounds of formula I in which one of the rings signifies a dioxane, pyrimidine or pyridazine ring and/or ring B stands for 1,4-phenylene will be readily apparent from the foregoing having regard to the known methods for the manufacture of such ring systems.

In general, in the manufacture of compounds of formula I which contain an ester group or a dioxane ring the esterification or the formation of the dioxane ring is advantageously carried out only as a last step. Examples for the manufacture of dioxanes provided by the invention are illustrated in Scheme 9. The pyrimidines and pyridazines provided by the invention can be obtained by firstly synthesizing the ring system according to known methods and subsequently introducing the alkenyl group or by using in the formation of the heterocyclic ring a compound which already contains the alkenyl group. The latter method is illustrated in more detail in Scheme 10 for certain pyrimidines.

Compounds of formula I in which $R^2$ signifies —OOCR can also be manufactured from compounds of formula I in which $R^2$ signifies —COR by Baeyer-Villiger oxidation with a peracid (e.g. perbenzoic acid) and subsequent conversion of the epoxide which is thereby simultaneously formed into the double bond according to the method described in Tetrahedron 36, 557 (1980).

Schemes 1, 2, 6 and 7 apply equally when the cyano group is replaced by alkyl, alkoxy or fluorine. However, it can be advantageous to manufacture compounds of formula I with different significances for $R^2$ according to a common Reaction Scheme and later to introduce the desired group $R^2$ in a manner known per se. Examples of these variants are illustrated in Scheme 11.

The starting materials required for the manufacture of fluoro compounds provided by the invention ($R^2$=fluorine) are known compounds or analogues of known compounds or can be obtained in a manner known per se from corresponding amines by diazotization with sodium nitrite and hydrochloric acid, conversion into the diazonium tetrafluoroborate with sodium tetrafluoroborate and subsequent heating. The amines can be obtained, for example, starting from the corresponding carboxylic acids by Hoffmann, Curtius or Schmidt degradation.

The manufacture of the compounds of formula I in which A stands for a group with 2 to 4 six-membered rings [or the preparation of the corresponding starting materials required in process variants (a)–(f)] can be carried out in an analogous manner to the manufacture of the bicyclic compounds described above in more detail.

The present invention is also concerned with trans-4-(trans-5-alkyl-m-dioxan-2-yl)cyclohexanecarbonitriles of the formula

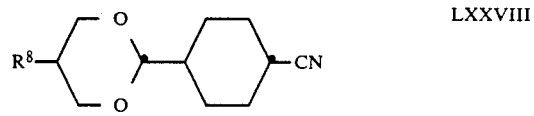

wherein $R^8$ signifies straight-chain $C_1$–$C_{12}$-alkyl,
as well as the manufacture of the compounds of formula LXXVIII above, liquid crystalline mixtures which contain these compounds and their use for electro-optical purposes.

The compounds of formula LXXVIII have at the same time a large positive anisotropy of the dielectric constants, a small optical anisotropy, low viscosity (especially when used in mixtures), low threshold potentials and short response times as well as an improved mesophase behaviour. Further, they have a high chemical stability and only slight conductivity, they are colourless and have a good miscibility with all customary liquid crystals and give a high contrast in indicating devices. The compounds provided by the invention are therefore very well suited for liquid crystalline dielectrics in electro-optical indicating devices such as, for example, in rotation cells and guest/host cells, especially in rotation cells.

Preferred compounds of formula LXXVIII are those in which $R^8$ signifies straight-chain $C_3$–$C_8$-alkyl.

The compounds of formula LXXVIII can be manufactured by reacting a compound of the formula

wherein $R^8$ has the above significance, with trans-4-cyanocyclohexanecarboxaldehyde or a suitable acetal thereof. The reaction can be carried out in an analogous manner to process variant (f) above.

The compounds of formula I and the compounds of formula LXXVIII can be used in the form of mixtures with other liquid crystalline or non-liquid crystalline substances such as, for example, with substances from the classes of Schiff's bases, azobenzenes, azoxybenzenes, phenyl benzoates, cyclohexanecarboxylic acid phenyl esters, cyclohexanecarboxylic acid cyclohexyl esters, biphenyls, terphenyls, phenylcyclohexanes, cinnamic acid derivatives, phenylpyrimidines, diphenylpyrimidines, cyclohexylphenylpyrimidines, phenyldioxanes, 2-cyclohexyl-1-phenylethanes, 1,2-dicyclohexylethanes and the like. Such substances are known to the person skilled in the art and many of them are, moreover, commercially available. When non-liquid crystalline components are used care should, however, be taken that additional liquid crystalline compounds are used in sufficient amount such that the total mixture has a sufficiently large mesophase range. Of course, the mixtures provided by the invention can also contain at the same time one or more compounds of formula I and one or more compounds of formula LXXVIII.

Having regard to the favourable properties of the compounds of formula I and to their good miscibility, the mixtures provided by the invention can also consist solely of two or more compounds of formula I. The mixtures provided by the invention therefore conveniently contain about 1–100 wt. %, preferably about 5–70 wt. % and particularly about 10–50 wt. % of compounds of formula I. Besides one or more compounds of formula I the mixtures provided by the invention contain, optionally, preferably one or more compounds of the formula

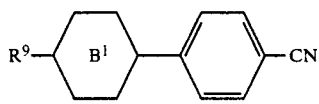

LXXX

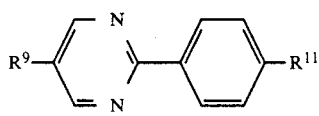

LXXXI

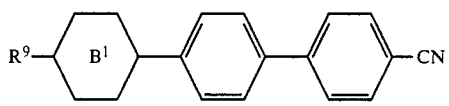

LXXXII

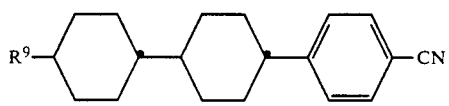

LXXXIII

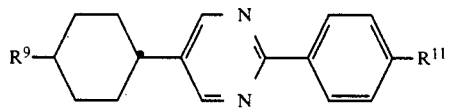

LXXXIV

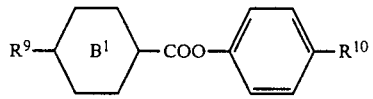

LXXXV

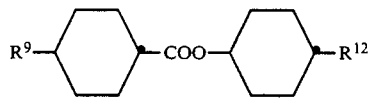

LXXXVI

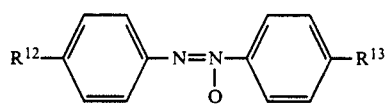

LXXXVII

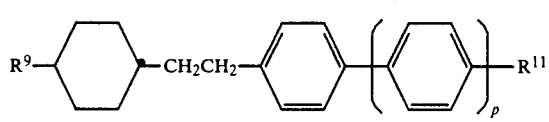

LXXXVIII

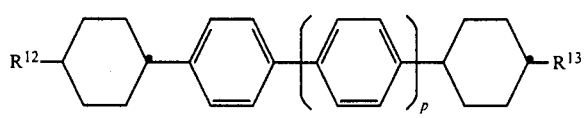

LXXXIX

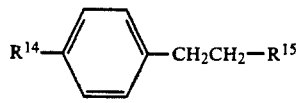

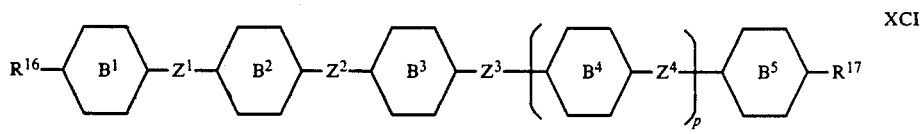

wherein ring $B^1$ denotes 1,4-phenylene or trans-1,4-cyclohexylene, $R^9$ denotes straight-chain $C_2$-$C_7$-alkyl, $R^{10}$ denotes cyano or straight-chain $C_1$-$C_6$-alkoxy, $R^{11}$ denotes cyano or straight-chain $C_1$-$C_7$-alkyl or $C_1$-$C_7$-alkoxy and $R^{12}$ and $R^{13}$ denote straight-chain $C_1$-$C_7$-alkyl; p stands for 0 or 1; $R^{14}$ signifies trans-4-alkylcyclohexyl, 4'-alkyl-4-biphenylyl, p-(trans-4-alkylcyclohexyl)phenyl, 2-(trans-4-alkylcyclohexyl)ethyl or p-[2-(trans-4-alkylcyclohexyl)ethyl]phenyl and $R^{15}$ signifies trans-4-alkylcyclohexyl, or $R^{14}$ signifies trans-4-alkylcyclohexyl and $R^{15}$ signifies p-(trans-4-alkylcyclohexyl)phenyl, p-[2-(trans-4-alkylcyclohexyl)ethyl]phenyl or 4'-(trans-4-alkylcyclohexyl)-4-biphenyl, or $R^{14}$ signifies p-alkylphenyl and $R^{15}$ signifies p-[2-(trans-4-alkylcyclohexyl)ethyl]phenyl, and the alkyl groups in $R^{14}$ and $R^{15}$ are straight-chain $C_1$-$C_7$-alkyl; one of the symbols $Z^1$ and $Z^2$ represents —COO— or —COOC— and the remainder of the symbols $Z^1$, $Z^2$, $Z^3$ and $Z^4$ represent single covalent bonds or one of these symbols also represents —CH$_2$CH$_2$—; the rings $B^1$ and $B^5$ in formula XCI denotes a group of the formula

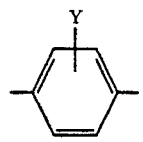

XCII or trans-1,4-cyclohexylene; the rings $B^2$, $B^3$ and $B^4$ represent a group of formula XCII or, insofar as they are not linked with at least one of the other two of these rings by a single covalent bond, also trans-1,4-cyclohexylene; Y signifies hydrogen or on one of the rings of formula XCII, which is not linked with a further ring via a single covalent bond, also fluorine, chlorine or methyl; $R^{16}$ and $R^{17}$ denote straight-chain $C_1$-$C_7$-alkyl or on a ring of formula XCII also straight-chain $C_1$-$C_7$-alkoxy.

The compounds of formulae LXXX–XC are known or can be prepared from known compounds by conventional techniques.

The esters of formula XCI are novel, but they can be obtained according to esterification methods which are known per se. The starting materials required for the preparation of the esters of formula XCI are known or are analogues of known compounds and can be prepared according to known methods.

The mixtures with compounds of formula LXXVIII contain, besides one or more compounds of formula LXXVIII, preferably one or more compounds of formulae LXXX–XCI. The amount of compounds of formula LXXVIII conveniently amounts to about 1–50 wt. %, preferably about 5–30 wt. %.

Further, the mixtures provided by the invention can contain suitable optically active compounds (e.g. optically active biphenyls) and/or dichroic colouring substances (e.g. azo, azoxy or anthraquinone colouring substances). The amount of such compounds is determined by the solubility and the desired pitch, colour, extinction and the like. The amount of optically active compounds preferably amounts to a maximum of about 4 wt. % and the amount of dichroic colouring substances preferably amounts to a maximum of about 10 wt. %.

The manufacture of the liquid crystalline mixtures provided by the invention can be carried out in a manner known per se; for example, by heating a mixture of the ingredients to a temperature barely above the clearing point and subsequently cooling the mixture.

The manufacture of electro-optical devices which contain a mixture provided by the invention as the dielectric can also be carried out in a manner known per se; for example, by evacuating a suitable cell and introducing the mixture into the evacuated cell.

The invention is also concerned with all novel compounds, mixtures, processes, uses and devices as described herein.

Mixtures 1–4 hereinafter are examples of preferred mixtures provided by the invention. $V_{10}$ denotes the threshhold potential for 10% transmission, $\eta$ denotes the viscosity (bulk viscosity) and $t_{on}$ denotes the switching-on time and $t_{off}$ denotes the switching-off time (in a rotation cell with $2.5 \cdot V_{10}$ and tilt angle 0°). The measurements were carried out at 22° C.

| Mixture 1 |
| --- |
| 19.0 wt. % of 4-ethoxy-1-[2-(trans-4-pentylcyclohexyl)-ethyl]benzene, |
| 3.5 wt. % of 4-cyano-4"-pentyl-p-terphenyl, |
| 3.5 wt. % of 4-cyano-4'-(trans-4-pentylcyclohexyl)-biphenyl, |
| 3.0 wt. % of p-[trans-4-(2-(trans-4-pentylcyclohexyl)-ethyl)cyclohexyl]benzonitrile, |
| 8.0 wt. % of 1-[2-(trans-4-butylcyclohexyl)ethyl]-4-(trans-4-pentylcyclohexyl)benzene, |
| 23.0 wt. % of p-[trans-4-(trans-1-butenyl)cyclohexyl]-benzonitrile, |
| 40.0 wt. % of p-[trans-4-(trans-1-pentenyl)cyclohexyl]-benzonitrile; |
| mp. < −20° C., cl.p. 78° C., nematic; $V_{10}$ = 2.18 V., $t_{on}$ = 23 ms, $t_{off}$ = 41 ms. |

| Mixture 2 |
| --- |
| 10.0 wt. % of p-(5-butyl-2-pyrimidinyl)benzonitrile, |
| 4.0 wt. % of p-(5-heptyl-2-pyrimidinyl)benzonitrile, |
| 9.0 wt. % of trans-4-butylcyclohexanecarboxylic acid p-pentyloxyphenyl ester, |
| 13.0 wt. % of trans-4-pentylcyclohexanecarboxylic acid p-propoxyphenyl ester, |
| 21.0 wt. % of 4-ethoxy-1-[2-(trans-4-propylcyclohexyl)- |

-continued

| Mixture 2 |
| --- |
| ethyl]benzene, |
| 4.0 wt. % of 4-cyano-4'-(trans-4-pentylcyclohexyl)biphenyl, |
| 6.0 wt. % of p-[5-(trans-4-ethylcyclohexyl)-2-pyrimidinyl]benzonitrile, |
| 6.5 wt. % of p-[trans-4-(trans-1-propenyl)cyclohexyl]benzonitrile, |
| 26.5 wt. % of p-[trans-4-(trans-1-butenyl)cyclohexyl]benzonitrile; |
| m.p. < −20° C., cl.p. 60° C., nematic; $\eta$ = 26.5 cp, $V_{10}$ = 1.50 V. |

| Mixture 3 |
| --- |
| 17.5 wt. % of p-(5-butyl-2-pyrimidinyl)benzonitrile, |
| 10.0 wt. % of p-(5-heptyl-2-pyrimidinyl)benzonitrile, |
| 6.5 wt. % of p-ethylbenzoic acid p'-cyanophenyl ester, |
| 8.0 wt. % of 4-cyano-4'-(trans-4-pentylcyclohexyl)biphenyl, |
| 10.0 wt. % of p-[5-(trans-4-ethylcyclohexyl)-2-pyrimidinyl]benzonitrile, |
| 14.5 wt. % of p-[trans-4-(trans-1-propenyl)cyclohexyl]benzonitrile, |
| 9.5 wt. % of p-[trans-5-(trans-1-pentenyl)-m-dioxan-2-yl]benzonitrile, |
| 24.0 wt. % of p-[trans-5-(trans-1-hexenyl)-m-dioxan-2-yl]benzonitrile; |
| m.p. about −10° C., cl.p. 80.4° C., nematic; $V_{10}$ = 1.31 V. |

| Mixture 4 |
| --- |
| 16.3 wt. % of p-(5-butyl-2-pyrimidinyl)benzonitrile, |
| 9.3 wt. % of p-(5-heptyl-2-pyrimidinyl)benzonitrile, |
| 6.1 wt. % of p-ethylbenzoic acid p'-cyanophenyl ester, |
| 7.0 wt. % of 4-ethyl-1-[2-(trans-4-propylcyclohexyl)ethyl]benzene, |
| 7.4 wt. % of 4-cyano-4'-(trans-4-pentylcyclohexyl)biphenyl, |
| 9.3 wt. % of p-[5-(trans-4-ethylcyclohexyl)-2-pyrimidnyl]benzonitrile, |
| 13.5 wt. % of p-[trans-4-(trans-1-propenyl)cyclohexyl]benzonitrile, |
| 8.8 wt. % of p-[trans-4-(trans-1-pentenyl)-m-dioxan-2-yl]benzonitrile, |
| 22.3 wt. % of p-[trans-5-(trans-1-hexenyl)-m-dioxan-2-yl]benzonitrile; |
| m.p. < −20° C., cl.p. 72° C., nematic; $V_{10}$ = 1.29 V. |

The following examples illustrate the manufacture of the inventive compounds. In the examples, C denotes a crystalline phase, S denotes a smectic phase, $S_B$ denotes a smectic B phase, N denotes a nematic phase and I denotes the isotropic phase. Unless otherwise stated, percentages and ratios relating to solvent mixtures are expressed in volume, purity data determined by gas chromatography are expressed in area % and the remaining percentages and ratios are expressed in weight, temperatures are in degrees Celsius (°C.), normal pressure is about 1 atmosphere and room temperature is about 23° C. The petroleum ether is a well-known mixture of low-boiling hydrocarbons. Unless indicated otherwise, the examples were carried out as written. The term "working-up" means, in the case of working-up of a reaction mixture, extraction of the product from the reaction mixture or, in the case of working-up of a mother liquor, crystallization of further product from the concentrated mother liquor.

EXAMPLE 1

A solution of 7.1 mmol of ethylmagnesium bromide (prepared from 172 mg of magnesium and 530 μl of ethyl bromide) in 20 ml of absolute tetrahydrofuran was placed at −78° C. while gassing with argon in a sulphonation flask provided with a thermometer, dropping funnel and serum cap and treated in sequence with 3.6 ml of a 0.48M solution of dilithium tetrachlorocuprate in absolute tetrahydrofuran and with a solution of 500 mg of p-[trans-4-(3-acetoxy-trans-1-propenyl)cyclohexyl]benzonitrile in 10 ml of absolute tetrahydrofuran. After completion of the addition, the mixture was warmed to −15° C., stirred at this temperature for 1.5 hours, subsequently treated with 20 ml of saturated ammonium chloride solution and stirred at room temperature for a further 1 hour. The aqueous phase, which was now deep blue, was separated and extracted twice with 50 ml of diethyl ether each time. The organic phases were washed twice with 50 ml of water each time, dried over magnesium sulphate and concentrated. Low-pressure chromatography (0.5 bar) of the residue (0.4 g) on silica gel with ethyl acetate/petroleum ether (vol. 3:97) gave 375 mg of crude p-[trans-4-(trans-1-pentenyl)cyclohexyl]benzonitrile which, according to analysis by gas chromatography, was contaminated to 8.5% with p-[trans-4-(trans-1-pentenyl)cyclohexyl]propiophenone and to 4.0% with p-[trans-4-(1-vinylpropyl)cyclohexyl]benzonitrile. Treatment of this crude product with an excess of sodium borohydride in methanol at 0° C. (in order to reduce the propiophenone), working-up, low-pressure chromatography (0.5 bar) on silica gel with ethyl acetate/petroleum ether (vol. 1:9) and finally recrystallization from methanol at −78° C. gave p-[trans-4-(trans-1-pentenyl)cyclohexyl]benzonitrile in a purity of 98.6%; m.p. (C-N) 15.5° C., cl.p. (N-I) 57.0° C.

In the chromatographic separation of the crude product on silica gel with ethyl acetate/petroleum ether (vol. 1:9) there was obtained as a second fraction 1-(1-hydroxypropyl)-4-[trans-4-(trans-1-pentenyl)cyclohexyl]benzene which was dissolved in acetone at 0° C. and oxidized to the ketone by the addition of chromic acid (until the orange colour remained). The excess chromic acid was decomposed with isopropanol. After working-up and recrystallization, there was finally obtained pure p-[trans-4-(trans-1-pentenyl)cyclohexyl]propiophenone of melting point (C-N) 60.5° C. and clearing point (N-I) 75.0° C.

The p-[trans-4-(3-acetoxy-trans-1-propenyl)cyclohexyl]benzonitrile used as the starting material was prepared as follows:

(a) 10.4 g of triphenyl-methoxymethyl-phosphonium chloride were suspended in 60 ml of t-butyl methyl ether while gassing with argon in a sulphonation flask provided with a thermometer, mechanical stirrer, dropping funnel and solid substance addition tube and treated at −10° C. within 10 minutes with 3.6 g of solid potassium t-butylate. After completion of the addition, the mixture was stirred at −10° C. to 0° C. for a further 30 minutes and then the deep orange, heterogenous mixture was treated dropwise at 0° C. with a solution of 4.2 g of 4-(p-cyanophenyl)cyclohexanone in 50 ml of absolute tetrahydrofuran. The mixture was subsequently stirred at room temperature for a further 2 hours, then poured into 500 ml of hexane and filtered. Low-pressure chromatography (0.5 bar) of the concentrated residue (7.1 g) on silica gel with ethyl acetate/petroleum ether (vol. 5:95) gave 4.5 g (94%) of p-[4-(methoxymethylene)cyclohexyl]benzonitrile as a colourless oil; purity 95%, Rf-value (ethyl acetate/petroleum ether vol. 1:9) 0.30.

(b) A mixture of 4.2 g of p-[4-(methoxymethylene)cyclohexyl]benzonitrile and 100 ml of tetrahydrofuran/2N hydrochloric acid (vol. 4:1) was heated to reflux for 30 minutes in a round flask. The mixture was subsequently poured into 100 ml of water and extracted three times with 100 ml of diethyl ether each time. The organic phases were washed once with 100 ml of water, dried over magnesium sulphate and concentrated. There were obtained 3.9 g (100%) of 4-(p-cyanophenyl)cyclohexanecarboxaldehyde as a colourless oil which was used in the next step without further purification: trans/cis ratio about 3:1, Rf-value (ethyl acetate/petroleum ether vol. 3:7) 0.41. By recrystallization from hexane there could be obtained pure trans-4-(p-cyanophenyl)cyclohexanecarboxaldehyde; m.p. 57.1° C.

(c) A mixture of 3.9 g of the 4-(p-cyanophenyl)cyclohexanecarboxaldehyde obtained above and 272 mg of powdered potassium carbonate in 60 ml of ethanol was placed at room temperature while gassing with argon in a sulphonation flask provided with a solid substance addition tube and treated within 15 minutes with 7.6 g of solid ethoxycarbonylmethylene-triphenylphosphorane. The mixture was subsequently stirred at room temperature for 2 hours, then freed from ethanol on a rotary evaporator, the residue was taken up in 100 ml of water and extracted three times with 100 ml of methylene chloride each time. The organic phases were washed twice with 100 ml of water each time, dried over magnesium sulphate and concentrated. Low-pressure chromatography (0.5 bar) of the residue (12 g) on silica gel with toluene/petroleum ether/ethyl acetate (vol. 5:4:1) gave 5.2 g of a crystalline mass which, after crystallization from 500 ml of hexane, yielded 3.9 g (75%) of ethyl trans-3-[trans-4-(p-cyanophenyl)cyclohexyl]acrylate as colourless crystals of melting point 125° C.

(d) A solution 1.0 g of ethyl trans-3-[trans-4-(p-cyanophenyl)cyclohexyl]acrylate in 25 ml of methylene chloride was placed at −78° C. while gassing with argon in a sulphonation flask provided with a thermometer and serum cap and treated within 10 minutes with 15.0 ml of a 0.84M solution of diisobutylaluminium hydride in toluene. After completion of the addition, the mixture was warmed to −10° C., stirred at this temperature for further 30 minutes, poured into 100 ml of 0.2N sulphuric acid and extracted twice with 50 ml of methylene chloride each time. The organic phases were washed with 50 ml of water, dried over magnesium sulphate and concentrated. The residue (about 850 mg) was dissolved in 30 ml of methylene chloride and treated in sequence with 0.5 ml of acetic anhydride and 45 mg of 4-(dimethylamino)pyridine. The mixture was stirred at room temperature for 1 hour, then poured into 50 ml of saturated, aqueous copper sulphate solution and extracted twice with 50 ml of methylene chloride each time. The organic phases were washed twice with 50 ml of water each time, dried over magnesium sulphate and concentrated. Low-pressure chromatography (0.5 bar) of the residue (0.95 g) on silica gel with ethyl acetate/petroleum ether (vol. 1:9) gave 720 mg (71%) of p-[trans-4-(3-acetoxy-trans-1-propenyl)cyclohexyl]benzaldehyde; purity 99.9%, Rf-value (ethyl acetate/petroleum ether vol. 1:9) 0.31.

(e) A solution of 513 mg of hydroxylammonium chloride in 5 ml of water was placed while gassing with argon in a sulphonation flask provided with a mechanical stirrer and treated at room temperature with a solution of 2.0 g of p-[trans-4-(3-acetoxy-trans-1-propenyl)cyclohexyl]benzaldehyde in 10 ml of pyridine. The mixture was stirred for 1 hour and then treated in sequence with 350 mg of copper sulphate pentahydrate and a solution of 2.1 ml of triethylamine in 10 ml of methylene chloride. After the initially inky blue colour of the copper-pyridine complex had turned olive-green, a solution of 1.74 g of dicyclohexylcarbodiimide in 20 ml of methylene chloride was added. The mixture was subsequently stirred at room temperature for a further 3 hours and then filtered. The filtrate was poured into 100 ml of water and extracted three times with 100 ml of methylene chloride each time. The organic phases were washed twice with 50 ml of water each time, dried over magnesium sulphate and concentrated. Low-pressure chromatography (0.5 bar) of the residue (2.75 g) on silica gel with toluene/ethyl acetate (vol. 9:1) gave 2.26 g (114%) of p-[trans-4-(3-acetoxy-trans-1-propenyl)cyclohexyl]benzonitrile as colourless crystals which still contained some dicyclohexylcarbodiimide as the sole impurity. This material was processed without additional purification. Rf-value (toluene/ethyl acetate vol. 9:1) 0.33.

The following compound was manufactured in an analogous manner:

p-[Trans-4-(trans-1-butenyl)cyclohexyl]benzonitrile, m.p. (C-N) 44.2° C., cl.p. (N-I) 49.5° C.

EXAMPLE 2

A mixture of 235 mg of p-[trans-4-(trans-1-pentenyl)cyclohexyl]propiophenone (prepared according to Example 1), 0.161 ml of hydrazine hydrate, 5 ml of diethylene glycol and 5 ml of ethanol was heated to reflux for 30 minutes under an argon atmosphere in a round flask provided with a reflux condenser. The mixture was then treated with 195 mg of solid potassium hydroxide and subsequently gradually heated to 200° C., while distilling off the ethanol, and held at this temperature for 2 hours. The cooled mixture was poured into 50 ml of water and extracted three times with 50 ml of petroleum ether each time. The organic phases were washed three times with 50 ml of water each time, dried over magnesium sulphate and concentrated. Low-pressure chromatography (0.5 bar) of the residue with hexane on a short column of silica gel gave 185 mg (83%) of 4-propyl-1-[trans-4-(trans-1-pentenyl)cyclohexyl]benzene as a colourless liquid; purity 98.6%, m.p. (C-I) 7.0° C.

EXAMPLE 3

A mixture of 3.8 g of 4-(p-cyanophenyl)cyclohexanecarboxaldehyde (prepared according to Example 1), 10.3 g of propyltriphenylphosphonium bromide and 12.3 g of potassium carbonate in 200 ml of dioxan was heated to reflux for 25 hours while gassing with argon in a round flask provided with a reflux condenser. The cooled mixture was subsequently filtered and concentrated. The residue was taken up in 150 ml of water and extracted three times with 150 ml of diethyl ether each time. The organic phases were washed twice with 100 ml of water each time, dried over magnesium sulphate and concentrated. Low-pressure chromatography (0.5 bar) of the residue (10.5 g) with ethyl acetate/petroleum ether (vol. 3:97) gave 2.35 g (55%) of a colourless, semicrystalline mass which, according to analysis by gas chromatography, consisted of 80.3 wt. % of p-[trans-4-(cis-1-butenyl)cyclohexyl]benzonitrile, 17.5 wt. % of p-[trans-4-(trans-1-butenyl)cyclohexyl]benzonitrile and 2.2 wt. % of p-[cis-4-(cis-1-butenyl)cyclohexyl]benzonitrile. By additional low-pressure chromatography (0.5 bar) of this material on silica gel coated with 10% silver nitrate using ethyl acetate/petroleum ether (vol. 3:97) and by subsequent crystallization from methanol at −78° C. there could be isolated pure p-[trans-4-(trans-1-butenyl)cyclohexyl]benzonitrile; m.p. (C-N) 44.2° C., cl.p. (N-I) 49.5° C.

EXAMPLE 4

(a) 4.0 g of 4-(p-cyanophenyl)cyclohexanecarboxaldehyde (prepared according to Example 1) were dissolved in 50 ml of 0.1N methanolic potassium hydroxide solution while gassing with argon in a sulphonation flask provided with a thermometer and the solution was treated portionwise at 0° C. within 20 minutes with 711 mg of sodium borohydride. The mixture was stirred at 0° C. for a further 10 minutes, neutralized with 1N hydrochloric acid and concentrated on a rotary evaporator. The residue was taken up in 200 ml of water and extracted three times with 100 ml of methylene chloride each time. The organic phases were washed twice with 100 ml of water each time, dried over magnesium sulphate and concentrated. A single crystallization of the residue (4.2 g) from 90 ml of ethyl acetate/petroleum ether (vol. 1:2) at 0° C. gave 3.27 g (77%) of p-[trans-4-(hydroxymethyl)cyclohexyl]benzonitrile as colourless crystals of melting point 109.8° C.; purity 99.4%.

(b) A solution of 3.0 g of p-[trans-4-(hydroxymethyl)cyclohexyl]benzonitrile in 5 ml of pyridine was placed at 0° C. while gassing with argon in a sulphonation flask provided with a mechanical stirrer, thermometer and dropping funnel and treated within 5 minutes with a solution of 4.4 g of p-tosyl chloride in 10 ml of pyridine. After completion of the addition, the cooling bath was removed and the mixture was stirred at room temperature for 15 hours. The mixture was freed from pyridine on a rotary evaporator and the residue was taken up in 100 ml of water and extracted three times with 100 ml of methylene chloride each time. The organic phases were washed twice with 100 ml of water each time, dried over magnesium sulphate and concentrated. Low-pressure chromatography (0.5 bar) of the residue (5.0 g) on silica gel with ethyl acetate/petroleum ether (vol. 1:4) gave 4.35 g (95%) of p-[trans-4-(p-tosyloxymethyl)cyclohexyl]benzonitrile as colourless crystals; Rf-value (ethyl acetate/petroleum ether vol. 3:7) 0.38.

(c) A mixture of 3.8 g of p-[trans-4-(p-tosyloxymethyl)cyclohexyl]benzonitrile, 2.3 g of sodium iodide and 100 ml of acetone was heated to reflux for 15 hours while gassing with argon in a round flask provided with a reflux condenser. After filtration and concentration of the mixture on a rotary evaporator, the residue was taken up in 100 ml of water and extracted three times with 100 ml of diethyl ether each time. The organic phases were washed twice with 100 ml of water each time, dried over magnesium sulphate and concentrated. Low-pressure chromatography (0.5 bar) of the residue on silica gel with toluene gave 3.19 g (95%) of p-[trans-4-(iodomethyl)cyclohexyl]benzonitrile as colourless crystals; Rf-value (ethyl acetate/petroleum ether vol. 1:9) 0.30.

EXAMPLE 5

A suspension of 2.51 g of methyltriphenylphosphonium bromide in 80 ml of absolute tetrahydrofuran was placed at −20° C. while gassing with argon in a sulphonation flask provided with a dropping funnel and thermometer and treated with 7.6 ml of an about 0.8M solution of butyl lithium in hexane. After stirring at −20° C. for 30 minutes, a solution of 1.0 g of trans-4-(p-cyanophenyl)cyclohexanecarboxaldehyde in 10 ml of absolute tetrahydrofuran was added dropwise at −20° C. within 5 minutes to the yellow mixture, whereby the yellow colour disappeared. The mixture was now stirred at −20° C. for a further 30 minutes and then poured into 100 ml of water and extracted three times with 100 ml of diethyl ether each time. The organic phases were washed twice with 100 ml of water each time, dried over magnesium sulphate and concentrated. Low-pressure chromatography (0.5 bar) of the residue (2.3 g) on silica gel with ethyl acetate/petroleum ether (vol. 3:97) gave 897 mg (91%) of p-(trans-4-vinylcyclohexyl)benzonitrile as colourless crystals; purity 99.4%. By additional crystallization from 22 ml of methanol there was obtained p-(trans-4-vinylcyclohexyl)benzonitrile in a purity of 99.95%; m.p. (C-I) 56.4° C., cl.p. 28.5° C.

EXAMPLE 6

A suspension of 3.6 g of butyltriphenylphosphonium bromide in 40 ml of t-butyl methyl ether was placed at room temperature while gassing with argon in a sulphonation flask provided with a thermometer, mechanical stirrer, dropping funnel and solid substance addition tube, treated with 1.01 g of potassium t-butylate and stirred at room temperature for a further 1 hour. The deep orange, heterogeneous mixture was subsequently cooled to −60° C. and treated within 15 minutes with a solution of 1.28 g of trans-4-(p-cyanophenyl)cyclohexanecarboxaldehyde in 10 ml of :-butyl methyl ether. The mixture was stirred for a further 60 minutes while warming slowly to −30° C., then poured into 100 ml of water and extracted three times with 50 ml of diethyl ether each time. The organic phases were washed once with 50 ml of water, dried over magnesium sulphate and concentrated. Low-pressure chromatography (0.5 bar) of the residue (3.45 g) on silica gel with ethyl acetate/petroleum ether (vol. 3:97) gave 1.52 g (99%) of p-[trans-4-(1-pentenyl)cyclohexyl]benzonitrile (trans-1-pentenyl/cis-1-pentenyl ratio about 5:95) as a colourless oil; Rf-value (ethyl acetate/petroleum ether vol. 3:97) 0.19.

The following compounds were manufactured in an analogous manner:

p-[Trans-4-(1-propenyl)cyclohexyl]benzonitrile, p-[trans-4-(1-butenyl)cyclohexyl]benzonitrile,
p-[trans-4-(1-hexenyl)cyclohexyl]benzonitrile,
p-[trans-4-(1-heptenyl)cyclohexyl]benzonitrile.

EXAMPLE 7

A mixture of 3.79 g of p-[trans-4-(1-hexenyl)cyclohexyl]benzonitrile (prepared according to Example 6; trans-1-hexenyl/cis-1-hexenyl ratio about 5:95) and 758 mg of benzenesulphonic acid in 50 ml of 1,4-dioxan was boiled under reflux for 15 hours while gassing with argon in a round flask provided with a magnetic stirrer and reflux condenser. A further 379 mg of benzenesulphonic acid were subsequently added and the mixture was heated to reflux for a further 4 hours. The cooled mixture was then poured into 50 ml of 1N sodium hydroxide solution and extracted three times with 100 ml of hexane each time. The organic phases were washed twice with 50 ml of water each time, dried over magnesium sulphate and concentrated. Three-fold crystallization of the quantitatively obtained, equilibrated, olefine mixture (trans-1-hexenyl/cis-1-hexenyl ratio 80.4:19.6)

from methanol finally gave 1.74 g (46%) of p-[trans-4-(trans-1-hexenyl)cyclohexyl]benzonitrile (containing 0.3% of cis-1-hexenyl isomer) of melting point (C-N) 14.3° C. and cl.p. (N-I) 39.5° C. The mother liquors were not worked-up. However, if desired, these can be again equilibrated and the equilibrated mixture can be subjected to crystallization.

The following compounds were manufactured in an analogous manner:

p-[Trans-4-(trans-1-propenyl)cyclohexyl]benzonitrile; m.p. (C-N) 66.3° C., cl.p. (N-I) 73.0° C.,
-p-[trans-4-(trans-1-butenyl)cyclohexyl]benzonitrile; m.p. (C-N) 45.1° C., cl.p. (N-I) 51.8° C.,
p-[trans-4-(trans-1-pentenyl)cyclohexyl]benzonitrile; m.p. (C-N) 15.6° C., cl.p. (N-I) 58.5° C.,
p-[trans-4-(trans-1-heptenyl)cyclohexyl]benzonitrile; m.p. (C-N) 17.9° C., cl.p. (N-I) 49.2° C.

EXAMPLE 8

A mixture of 2.75 g of p-[trans-4-(erythro-1,2-dibromopentyl)cyclohexyl]benzonitrile and 20 ml of glacial acetic acid was treated at room temperature with 2.42 g of zinc powder while gassing with argon in a sulphonation flask provided with a mechanical stirrer and thermometer and then stirred for 2 hours, whereby the mixture warmed to 33° C. and the educt gradually passed into solution. The mixture was subsequently poured into 100 ml of water and extracted three times with 100 ml of petroleum ether each time. The organic phases were washed twice with 100 ml of water each time and once with 50 ml of saturated sodium hydrogen carbonate solution, dried over magnesium sulphate and concentrated. There were thus obtained 1.43 g (99%) of p-[trans-4-(trans-1-pentenyl)cyclohexyl]benzonitrile in a purity of 99.5%; m.p. (C-N) 15.6° C., cl.p. (N-I) 58.5° C.

The p-[trans-4-(erythro-1,2-dibromopentyl)cyclohexyl]benzonitrile used as the starting material was prepared as follows:

(a) A mixture of 1.51 g of 90% m-chloroperbenzoic acid and 3.0 g of powdered potassium carbonate in 60 ml of methylene chloride was placed at 0° C. while gassing with argon in a sulphonation flask provided with a thermometer, dropping funnel and mechanical stirrer and treated within 15 minutes with a solution of 2.0 g of p-[trans-4-(1-pentenyl)cyclohexyl]benzonitrile (prepared according to Example 6; trans-1-pentenyl/cis-1-pentenyl ratio about 5:95) in 20 ml of methylene chloride. The cooling bath was subsequently removed and the mixture was treated after a total of 75 minutes and 105 minutes with in each case a further 0.75 g of 90% m-chloroperbenzoic acid. The mixture was stirred at room temperature for a further 60 minutes, then poured into 50 ml of 10% (wt./vol.)sodium thiosulphate solution and extracted three times with 100 ml of methylene chloride each time. The organic phases were washed with 50 ml of saturated sodium hydrogen carbonate solution, dried over magnesium sulphate and concentrated. There were thus obtained 2.1 g (98%) of p-[trans-4-(1,2-epoxypentyl)cyclohexyl]benzonitrile (trans-1,2-epoxypentyl/cis-1,2-epoxypentyl ratio about 5:95) as a colourless oil; Rf-values (ethyl acetate/petroleum ether vol. 10:90): trans-1,2-epoxypentyl isomer 0.17, cis-1,2-epoxypentyl isomer 0.14.

(b) A solution of 2.46 g of triphenylphosphine in 30 ml of methylene chloride was placed at 0° C. while gassing with argon in a round flask provided with a dropping funnel and treated dropwise with an about 1M solution of bromine in methylene chloride until a faint yellow colour remained. The solution was subsequently concentrated cautiously on a rotary evaporator and then dried in a high vacuum. The crystalline residue obtained was suspended in 30 ml of benzene, treated with a solution of 2.1 g of p-[trans-4-(1,2-epoxypentyl)-cyclohexyl]benzonitrile in 10 of benzene and heated to reflux for 3 hours. Filtration of the warm solution on silica gel with toluene gave 3.0 g of crystalline crude product which, after low-pressure chromatography (0.5 bar) on silica gel with hexane/toluene (vol. 1:1), yielded 2.61 g (81%) of almost pure p-[trans-4-(erythro-1,2-dibromopentyl)cyclohexyl]benzonitrile as colourless crystals. By recrystallization from 90 ml of petroleum ether/ethyl acetate (vol. 2:1) there were finally obtained 2.09 g (65%) of very pure erythro dibromide; m.p. 140.9° C.

The following compounds were manufacture in an analogous manner:

p-[Trans-4-(trans-1-propenyl)cyclohexyl]benzonitrile; m.p. (C-N) 66.3° C., cl.p. (N-I) 73.0° C.,
p-[trans-4-(trans-1-butenyl)cyclohexyl]benzonitrile; m.p. (C-N) 45.1° C., cl.p. (N-I) 51.8° C.,
p-[trans-4-(trans-1-hexenyl)cyclohexyl]benzonitrile; m.p. (C-N) 14.4° C., cl.p. (N-I) 39.2° C.
p-[trans-4-(trans-1-heptenyl)cyclohexyl]benzonitrile; m.p. (C-N) 17.9° C., cl.p. (N-I) 49.2° C.

EXAMPLE 9

In an analogous manner to Examples 1, 5, 6 and 8, 4-[2-(p-cyanophenyl)ethyl]cyclohexanone was converted into trans-4-[2-(p-cyanophenyl)ethyl]cyclohexanecarboxaldehyde and the latter was converted into p-[2-(trans-4-(trans-1-alkenyl)cyclohexyl)ethyl]benzonitriles.

The 4-[2-(p-cyanophenyl)ethyl]cyclohexanone used as the starting material was prepared as follows:

(a) 149 g of methoxymethyl-triphenylphosphonium chloride and 860 ml of t-butyl methyl ether were placed in a sulphonation flask at room temperature while stirring and gassing with nitrogen, the suspension was cooled to −10° C. and treated within 10 minutes with 51.6 g of potassium t-butylate. The suspension was stirred at −10° C. to 0° C. for a further 30 minutes and then treated dropwise within 45 minutes at 0° C. with a solution of 47.3 g of 4,4-ethylenedioxycyclohexanone in 720 ml of tetrahydrofuran. The orange suspension was stirred at room temperature for a further 2 hours, then poured into 5 l of hexane, stirred for 10 minutes and suction filtered. The filtrate was concentrated in vacuo and the resulting yellow-brownish oil (104.1 g) was treated with 500 ml of hexane and suction filtered. The filtrate was concentrated in vacuo, 61.7 g of a yellow-brownish oil being obtained. Chromatographic separation of this crude product on silica gel with methylene chloride/acetone (vol. 98:2 and 95:5) finally gave 53.5 g of 1,1-ethylenedioxy-4-(methoxymethylene)cyclohexane as a colourless oil.

(b) A mixture of 28.2 g of 1,1-ethylenedioxy-4-(methoxymethylene)cyclohexane, 770 ml of glacial acetic acid and 385 ml of water was heated to reflux for 1 hour while gassing with nitrogen in a round flask. Thereafter the yellowish clear solution was cooled to room temperature, diluted with 800 ml of water and extracted three times with 700 ml of methylene chloride each time. The organic phases were washed twice with 500 ml of 10% (wt./vol,) sodium carbonate solution each time, dried over sodium sulphate, filtered and concentrated. Chromatographic separation of the resulting brownish liquid (18.5 g) on silica gel with methylene chloride as the eluent finally gave 16.7 g of 4-formylcyclohexanone as a brownish liquid.

(c) 63.3 g of p-cyanobenzyl-triphenylphosphonium chloride, 17.2 g of potassium t-butylate and 195 ml of ethylene glycol dimethyl ether were placed while stirring and gassing with nitrogen in a sulphonation flask, whereby the internal temperature rose to 44° C. The brown suspension was cooled to 0° C. and treated within 2 minutes with a solution of 16.7 g of 4-formylcyclohexanone in 100 ml of ethylene glycol dimethyl ether. The cooling bath was then removed and the mixture was stirred at room temperature for a further 3.5 hours. The suspension was subsequently poured into 500 ml of water and extracted three times with 600 ml of methylene chloride each time. The organic phases were washed twice with 500 ml of 10% (wt./vol.) sodium chloride solution each time, dried over sodium sulphate, filtered and concentrated, there being obtained 76.9 g of a brownish paste. Chromatographic separation of this crude product on silica gel with methylene chloride as the eluent gave 33.0 g of 4-[2-(p-cyanophenyl)vinyl]cyclohexanone as a yellow-brownish oil.

(d) A mixture of 33.0 g of 4-[2-(p-cyanophenyl)vinyl]-cyclohexanone, 520 ml of toluene, 260 ml of ethanol and 3.2 g of palladium/carbon-(5%) was placed at room temperature in a round flask provided with a magnetic stirrer and the mixture was hydrogenated until the hydrogen uptake came to a standstill. The black suspension was subsequently suction filtered (rinsing with toluene) and the filtrate was concentrated in vacuo. The resulting, slightly turbid, yellowish oil (34.1 g) was separated by chromatography on silica gel. Elution with methylene chloride/hexane (vol. 1:1), methylene chloride/hexane (vol. 8:2) and methylene chloride yielded 25.6 g of a yellowish oil which was crystallized from t-butyl methyl ether. There were thus obtained 22.6 g of 4-[2-(p-cyanophenyl)ethyl]cyclohexanone as colourless crystals of melting point 62.5°-64.3° C.

The following compounds were manufactured in an analogous manner:

p-[2-(Trans-4-(trans-1-propenyl)cyclohexyl)ethyl]benzonitrile; m.p. (C-I) 61.3° C., cl.p. (N-I) 54.2° C., p-[2-(trans-4-(trans-1-butenyl)cyclohexyl)ethyl]benzonitrile; m.p. (C-I) 42.6° C., cl.p. (N-I) 39.7° C., p-[2-(trans-4-(trans-1-pentenyl)cyclohexyl)ethyl]benzonitrile; m.p. (C-N) 25.1° C., cl.p. (N-I) 47.5° C., p-[2-(trans-4-(trans-1-hexenyl)cyclohexyl)ethyl]benzonitrile; m.p. (C-N) 16.8° C. and 19.7° C. (two modifications), cl.p. (N-I) 34.6° C., p-[2-(trans-4-(trans-1-heptenyl)cyclohexyl)ethyl]benzonitrile; m.p. (C-N) 31.6° C., cl.p. (N-I) 43.6° C.

EXAMPLE 10

A mixture of 200 mg of trans-4-(trans-1-pentenyl)cyclohexanol, 245.9 mg of trans-4-pentylcyclohexanecarboxylic acid, 293 mg of dicyclohexylcarbodiimide, 14.16 mg of 4-(dimethylamino)pyridine and 3 ml of methylene chloride was stirred at room temperature for 25 hours. The mixture was subsequently diluted with diethyl ether, the precipitated urea was filtered off and the filtrate was concentrated. The residue was taken up in 40 ml of methylene chloride and washed with 5% hydrochloric acid, sodium hydrogen carbonate solution and sodium chloride solution. The aqueous phases were back-extracted with methylene chloride. The organic phases were dried over magnesium sulphate, filtered and concentrated. Low-pressure chromatography of the resulting, white residue (450 mg) on silica gel with diethyl ether/petroleum ether (vol. 3:97) gave 348 mg of white, transparent needles which were recrystallized from 20 ml of methanol. There were thus obtained 289 mg of trans-4-pentylcyclohexanecarboxylic acid trans-4-(trans-1-pentenyl)cyclohexyl ester; m.p. (C-S) 39.8° C., cl.p. (S-I) 66.5° C.

The trans-4-(trans-1-pentenyl)cyclohexanol used as the starting material was prepared as follows:

(a) 261.2 g of methoxymethyl-triphenylphosphonium chloride were suspended in 550 ml of t-butyl methyl ether and treated at −10° C. with 90.53 g of potassium t-butylate. The cooling bath was removed and the mixture was stirred at room temperature for 1 hour. The suspension was subsequently treated slowly at −10° C. with a solution of 70 g of 4,4-ethylenedioxycyclohexanone in 350 ml of tetrahydrofuran, stirred at room temperature for 1 hour, then treated with water and extracted three times with diethyl ether. The organic phases were washed twice with water and the aqueous phases were back-extracted with diethyl ether. The combined organic phases were dried over magnesium sulphate and concentrated. The crystalline residue obtained was dissolved in ethyl acetate, diluted with petroleum ether, filtered and freed from solvent. Distillation of the resulting, yellow oil (100 g) gave in the main run (71° C./0.20-0.17 Torr) 75.28 g (91.17%) of 1,1-ethylenedioxy-4-(methoxymethylene)cyclohexane as a clear, colourless liquid.

(b) A mixture of 10.55 g of 1,1-ethylenedioxy-4-(methoxymethylene)cyclohexane, 130 ml of water and 200 ml of glacial acetic acid was heated to reflux for 1 hour. The solvent was subsequently distilled off on a rotary evaporator and the distillate was extracted twice with methylene chloride. The distillation residue (a yellow oil) was diluted with 200 ml of water, neutralized with sodium carbonate solution and extracted three times with methylene chloride. The organic phases were washed with saturated sodium carbonate solution and the aqueous phases were back-extracted with methylene chloride. The organic phases were dried over magnesium sulphate and evaporated. Distillation of the residual, yellow oil gave 6.7 g (93%) of 4-formylcyclohexanone at 70° C./0.15 Torr.

(c) A solution of 36.72 g of triphenylphosphine in 200 ml of methylene chloride was treated slowly at −20° C. with 23.22 g of carbon tetrabromide and stirred for a further 10 minutes. Subsequently, the mixture was added dropwise by means of a cannula to a solution, cooled to −60° C., of 6.30 g of 4-formylcyclohexanone in 100 ml of methylene chloride. The mixture was stirred at −60° C. for a further 15 minutes and then partitioned in water/methylene chloride. The aqueous phases were extracted a further twice with methylene chloride. The organic phases were washed twice with water, dried over magnesium sulphate and evaporated. Low-pressure chromatography of the resulting, pale yellow oil (16 g) on silica gel with ethyl acetate/petroleum ether (vol. 10:90) gave 12.08 g (85.8%) of 4-(2,2-dibromovinyl)cyclohexanone as a pale yellow liquid.

(d) A mixture of 2 g of 4-(2,2-dibromovinyl)cyclohexanone, 3.43 g of ethylene glycol, 0.202 g of p-toluenesulphonic acid and 240 ml of benzene was boiled at reflux for 5 hours with separation of water. The mixture was subsequently treated with potassium carbonate, stirred for a short time and left to stand overnight. The mixture was then filtered and the filtrate was freed from solvent on a rotary evaporator. The residue was taken up in 200 ml of methylene chloride and washed twice with dilute sodium hydroxide solution and once with water. The aqueous phases were back-extracted with methylene chloride. The organic phases were dried over magnesium sulphate, filtered and evaporated. There were thus obtained 14 g of 1,1-ethylenedioxy-4-(2,2-dibromovinyl)cyclohexane as a light yellow, crystallizing liquid.

(e) A solution of 14 g of 1,1-ethylenedioxy-4-(2,2-dibromovinyl)cyclohexane in 70 ml of tetrahydrofuran was cooled to $-20°$ C. and treated slowly at this temperature with 76.62 ml of a 1.4M solution of butyl lithium in hexane (exothermic reaction). The cooling bath was removed and the mixture was left to warm to 20° C. within about 20 minutes. The mixture was subsequently treated with 150 ml of water and extracted three times with diethyl ether. The organic phases were washed twice with water and the wash-water was back-extracted with diethyl ether. The organic phases were dried over magnesium sulphate, filtered and evaporated. Low-pressure chromatography of the resulting, yellow liquid (8 g) on silica gel with ethyl acetate/petroleum ether (vol. 7:93) gave 6.5 g (91%) of 4-ethynyl-1,1-ethylenedioxycyclohexane as a clear liquid.

(f) A solution of 6.5 g of 4-ethynyl-1,1-ethylenedioxycyclohexane in 40 ml of tetrahydrofuran was treated at $-20°$ C. with 39.1 ml of a 1.4M solution of butyl lithium in hexane. Subsequently, the mixture was treated at 0° C. with 60 ml of hexamethylphosphoric acid triamide (brief temperature rise to 26° C.) and then dropwise with 6.5 ml of propyl iodide. The cooling bath was removed and the mixture was left to warm to room temperature. A white precipitate formed. After 30 minutes, the mixture was treated with 150 ml of water and extracted three times with hexane. The organic phases were washed three times with water and the wash-water was back-extracted with hexane. The organic phases were dried over magnesium sulphate, filtered and freed from solvent on a rotary evaporator. Low-pressure chromatography of the resulting, yellow liquid (9 g) on silica gel with ethyl acetate/petroleum ether (vol. 10:90) and treatment with active carbon gave 6.23 g (76.5%) of 1,1-ethylenedioxy-4-(1-pentynyl)cyclohexane as a light pale yellow liquid.

(g) A solution of 4.5 g of 1,1-ethylenedioxy-4-(1-pentynyl)cyclohexane in 54 ml of tetrahydrofuran was treated dropwise with about 50 ml of pre-condensed ammonia in a sulphonation flask provided with a magnetic stirrer. The mixture was subsequently treated portionwise at $-78°$ C. within 7 hours with 1.3 g of sodium. 1.5 hours after the last addition the ammonia was removed by evaporation and the mixture was neutralized with 25% hydrochloric acid and left to stand overnight. The mixture was then partitioned three times in water/diethyl ether. The aqueous phases were back-extracted with diethyl ether. The organic phases were dried over magnesium sulphate and then freed from solvent on a rotary evaporator. The resulting, pale yellow liquid (3.8 g) was treated with 200 ml of acetone and 0.1 ml of concentrated sulphuric acid. The mixture was heated to reflux for 10 minutes, then treated with water and freed from acetone on a rotary evaporator. The residue was partitioned three times in methylene chloride/water. The aqueous phases were back-extracted with methylene chloride. The organic phases were dried over magnesium sulphate and evaporated. Chromatographic separation of the resulting, yellow liquid (3.5 g) on silica gel with ethyl acetate/petroleum ether (vol. 7:93) gave 3.0 g (83.5%) of 4-(trans-1-pentenyl)cyclohexanone as a pale yellow liquid.

(h) 1.63 g of 4-(trans-1-pentenyl)cyclohexanone were dissolved in 8 ml of diethyl ether and 14 ml of ethanol. Subsequently, the solution was treated dropwise with about 70 ml of ammonia and portionwise with lithium wire until the colour of the mixture remained constant for 1.5 hours (about 1.3 g of lithium). Thereafter, the ammonia was removed by evaporation and the mixture was made acid with ammonium chloride and hydrochloric acid and left to stand for 3 days. The mixture was then partitioned in diethyl ether/water and the aqueous phases were back-extracted with diethyl ether. The organic phases were dried over magnesium sulphate, filtered and freed from solvent on a rotary evaporator. Low-pressure chromatography of the resulting, yellow oil on silica gel with ethyl acetate/petroleum ether (vol. 10:90) gave 1.47 g (89.1%) of trans-4-(trans-1-pentenyl)cyclohexanol as a light yellow, viscous oil.

The following compounds were manufactured in an analogous manner:

Trans-4-propylcyclohexanecarboxylic acid trans-4-(trans-1-pentenyl)cyclohexyl ester; m.p. (C-S) 23.8° C., cl.p. (S-I) 50.7° C., trans-4-butylcyclohexanecarboxylic acid trans-4-(trans-1-pentenyl)cyclohexyl ester; m.p. (C-S) 26.2° C., cl.p. (S-I) 65.0° C.

EXAMPLE 11

A mixture of 800 mg of trans-4-(trans-1-pentenyl)cyclohexanecarboxylic acid, 675.64 mg of p-ethoxyphenol, 1.01 g of dicyclohexylcarbodiimide and 49.79 mg of 4-(dimethylamino)pyridine was suspended in 14.5 ml of methylene chloride and stirred at room temperature for 20 hours. The mixture was subsequently diluted with diethyl ether, the precipitated urea was filtered off and the filtrate was concentrated. The residue was taken up in hexane and washed with dilute hydrochloric acid, sodium hydrogen carbonate solution and water. The aqueous phases were back-extracted twice with hexane. The organic phases were dried over magnesium sulphate and evaporated. Low-pressure chromatography of the resulting residue on silica gel with ethyl acetate/petroleum ether (vol. 3:97) gave 1.080 g (83.8%) of trans-4-(trans-1-pentenyl)cyclohexanecarboxylic acid p-ethoxyphenyl ester. After recrystallization from 40 ml of hexane, there were finally obtained 880 mg of product in the form of transparent crystals; m.p. (C-N) 57.2° C., cl.p. (N-I) 93.1° C.

The trans-4-(trans-1-pentenyl)cyclohexanecarboxylic acid used as the starting material was prepared as follows:

(a) 7 g of methoxymethyl-triphenylphosphonium chloride were suspended in 35 ml of t-butyl methyl ether and treated at $-20°$ C. with 2.43 g of potassium t-butylate. The mixture was stirred at room temperature for 1 hour, then treated dropwise at $-20°$ C. with a solution of 2 g of 4-(trans-1-pentenyl)cyclohexanone in 18 ml of tetrahydrofuran and stirred at room temperature for a further 1 hour. The mixture was subsequently treated with water and extracted three times with 50 ml of diethyl ether each time. The extracts were washed with water and the wash-water was back-extracted with diethyl ether. The organic phases were dried over magnesium sulphate and freed from solvent. The residue was dissolved in ethyl acetate and the solution was diluted with petroleum ether, freed from precipitated triphenylphosphine oxide by filtration and again concentrated. This procedure for the separation of triphenylphosphine oxide was repeated a futher twice and the resulting crude product of 1-(methoxymethylene)-4-(trans-1-pentenyl)cyclohexane was processed without additional purification.

(b) 2.75 g of 1-(methoxymethylene)-4-(trans-1-pentenyl)cyclohexane [crude product from paragrah (a)] were heated to reflux for 30 minutes with 100 ml of tetrahydrofuran/2N hydrochloric acid (vol. 4:1) and then stirred at room temperature overnight. The mixture was subsequently treated with 100 ml of water and extracted three times with 100 ml of diethyl ether each time. The extracts were washed with dilute sodium hydrogen carbonate solution and water and the aqueous phases were back-extracted with diethyl ether. The organic phases were dried over magnesium sulphate and evaporated. Low-pressure chromatography of the resulting, yellowish liquid (2.5 g) on silica gel with petroleum ether and ethyl acetate/petroleum ether (vol. 3:97) gave 1.65 g (76%) of 4-(trans-1-pentenyl)cyclohexanecarboxaldehyde.

(c) A solution of 1.6 g of 4-(trans-1-pentenyl)cyclohexanecarboxaldehyde in 120 ml of acetone was cooled to −10° C., treated dropwise with 8N chromic acid (about 10 ml) until the colour of the mixture remained brown-orange and stirred for 1 hour. Excess chromic acid was reduced by the addition of isopropanol. The green solution was subsequently partitioned three times in water/methylene chloride. The organic extracts were washed twice with water and the wash-water was back-extracted with methylene chloride. The organic phases were dried over magnesium sulphate and evaporated. The pale brown crystalline residue (2.01 g) was dissolved partially in 20 ml of petroleum ether. Undissolved residue was filtered off and the filtrate was evaporated. Recrystallization of the resulting residue from 60 ml of petroleum ether at −78° C. gave 866 mg (49.5%) of 4-(trans-1-pentenyl)cyclohexanecarboxylic acid as white crystals.

(d) A mixture of 1.29 g of 4-(trans-1-pentenyl)cyclohexanecarboxylic acid and 20 ml of a 11% (wt./vol.) solution of potassium hydroxide in diethylene glycol was boiled at reflux for 20 hours while gassing with argon. The mixture was subsequently made slightly acid with 25% hydrochloric acid and partitioned three times in water/methylene chloride. The organic extracts were washed twice with water and the wash-water was back-extracted with methylene chloride. The organic phases were dried over magnesium sulphate and freed from solvent on a rotary evaporator. Recrystallization of the resulting, dark brown, crystallizing oil (1.17 g) from 50 ml of petroleum ether at −78° C. gave 0.44 g of trans-4-(trans-1-pentenyl)cyclohexanecarboxylic acid as pale brown crystals. The mother liquor containing 0.695 g of crude cis/trans-4-(trans-1-pentenyl)cyclohexanecarboxylic acid was not worked-up.

EXAMPLE 12

A suspension of 6.64 g of methyltriphenylphosphonium bromide in 80 ml of t-butyl methyl ether was treated with 2.12 g of solid potassium t-butylate at −10° C. within 3 minutes while gassing with argon in a sulphonation flask provided with a mechanical stirrer. The mixture was stirred at room temperature for a further 1 hour, then treated at 0° C. within 5 minutes with a solution of 3.0 g of 3-[trans-4-(p-cyanophenyl)cyclohexyl]propionaldehyde in 20 ml of t-butyl methyl ether and stirred at room temperature for a further 15 minutes. The mixture was subsequently partitioned three times in diethyl ether/water. The organic extracts were washed twice with water, dried over magnesium sulphate, filtered and evaporated. In order to separate triphenylphosphine oxide, the residue was dissolved in ethyl acetate and the solution was diluted with petroleum ether, filtered and evaporated. Chromatographic separation of the resulting, pale brown oil (4.38 g) on silica gel with ethyl acetate/petroleum ether (vol. 3:97) gave 2.83 g of white crystals. Recrystallization from methanol and working-up of the mother liquor finally gave a total of 2.116 g of p-[trans-4-(3-butenyl)cyclohexyl]benzonitrile as white crystals; m.p. (C-N) 49.5° C., cl.p. (N-I) 52.5° C.

The 3-[trans-4-(p-cyanophenyl)cyclohexyl]propionaldehyde used as the starting material was prepared as follows:

(a) A suspension of 29.0 g of methoxymethyl-triphenylphosphonium-chloride in 200 ml of t-butyl methyl ether was treated with 9.7 g of potassium t-butylate at −10° C. within 3 minutes while gassing with argon in a sulphonation flask provided with a mechanical stirrer. The orange suspension was stirred at about 0° C. for 1 hour, then treated dropwise at −10° C. within 10 minutes with a solution of 12.0 g of trans-4-(p-cyanophenyl)cyclohexanecarboxaldehyde in 90 ml of t-butyl methyl ether and stirred at 0° C. for a further 45 minutes. The mixture was subsequently partitioned three times in diethyl ether/water. The organic extracts were washed twice with water, dried over magnesium sulphate, filtered and evaporated. In order to separate triphenylphosphine oxide, the residue was diluted with petroleum ether, filtered and evaporated. Chromatographic separation of the yellowish, crystalline residue (16.3 g) on silica gel with ethyl acetate/petroleum ether (vol. 5:95) gave 10.1 g (74%) of p-[trans-4-(2-methoxyvinyl)cyclohexyl]benzonitrile as white crystals.

(b) A solution of 10.1 g of p-[trans-4-(2-methoxyvinyl)cyclohexyl]benzonitrile in 200 ml of tetrahydrofuran/2N hydrochloric acid (vol. 4:1) was heated to reflux for 1 hour while stirring. The mixture was subsequently partitioned three times in diethyl ether/water. The organic extracts were washed twice with water, dried over magnesium sulphate, filtered and evaporated, there being obtained 9.8 g of 2-[trans-4-(p-cyanophenyl)cyclohexyl]acetaldehyde as a light yellowish, crystalline residue.

(c) A suspension of 22.2 g of methoxymethyl-triphenylphosphonium chloride in 150 ml of t-butyl methyl ether was treated with 7.4 g of solid potassium t-butylate at 0° C. within 3 minutes while gassing with argon in a sulphonation flask provided with a mechanical stirrer. The orange suspension was stirred at 0° C. for 1 hour and then treated dropwise within 10 minutes with a solution of 9.8 g of 2-[trans-4-(p-cyanophenyl)cyclohexyl]acetaldehyde in 100 ml of tetrahydrofuran. Subsequently, the suspension was left to warm slowly to room temperature while stirring. After 15 hours, the suspension was partitioned three times in diethyl ether/water. The organic extracts were washed twice with water, dried over magnesium sulphate, filtered and evaporated. In order to separate triphenylphosphine oxide, the residue was dissolved in ethyl acetate and the solution was diluted with petroleum ether, filtered and evaporated. Chromatographic separation of the resulting, yellowish oil (13.7 g) on silica gel with ethyl acetate/petroleum ether (vol. 5:95) gave 10.5 g (96%) of p-[trans-4-(3-methoxy-2-propenyl)cyclohexyl]benzonitrile as a colourless oil.

(d) A solution of 10.5 g of p-[trans-4-(3-methoxy-2-propenyl)cyclohexyl]benzonitrile in 200 ml of tetrahydrofuran/2N hydrochloric acid (vol. 4:1) was heated to reflux for 45 minutes while stirring. The mixture was then partitioned three times in diethyl ether/water. The organic extracts were washed twice with water, dried over magnesium sulphate, filtered and evaporated. Chromatographic separation of the white, crystalline residue, (9.9 g) on silica gel with ethyl acetate/petroleum ether (vol. 10:90 and 30:70) finally gave 9.4 g (95%) of 3-[trans-4-(p-cyanophenyl)cyclohexyl]propionaldehyde as white crystals.

EXAMPLE 13

A solution of 9.54 g of p-[trans-4-(erythro-3,4-dibromopentyl)cyclohexyl]benzonitrile in 100 ml of glacial acetic acid was treated with 9.8 g of zinc powder while gassing with argon in a round flask provided with a magnetic stirrer. The mixture was stirred at room temperature for 30 minutes and then partitioned three times in petroleum ether/water. The organic extracts were washed twice with water, dried over magnesium sulphate, filtered and concentrated. Chromatographic separation of the oily residue (5.56 g) on silica gel coated with silver nitrate (prepared by suspending 300 g of silica gel in 500 ml of a 0.2M solution of silver nitrate in acetonitrile, subsequently filtering and drying the residue) using diethyl ether/hexane (vol. 1:9) as the eluent gave 3.2 g of crude product as white crystals. After recrystallization from 80 ml of methanol, 1.65 g (28%) of p-[trans-4-(trans-3-pentenyl)cyclohexyl]benzonitrile were obtained as white crystals. The mother liquor and the impure fractions from the chromatographic separation were combined and again purified on silica gel coated with silver nitrate using diethyl ether/hexane (vol. 1:9) as the eluent. Recrystallization of the resulting, crystalline product (1.5 g) from 40 ml of methanol gave a further 0.65 g of p-[trans-4-(trans-3-pentenyl)cyclohexyl]benzonitrile as white crystals; m.p. (C-N) 59.8° C., cl.p. (N-I) 73.7° C.

The p-[trans-4-(erythro-3,4-dibromopentyl)cyclohexyl]benzonitrile used as the starting material was prepared as follows:

(a) A suspension of 14.8 g of ethyltriphenylphosphonium bromide in 150 ml of t-butyl methyl ether was treated with 4.54 g of solid potassium t-butylate at −10° C. within 5 minutes while gassing with argon in a sulphonation flask provided with a mechanical stirrer. The suspension was stirred at room temperature for 1 hour, then treated dropwise at 0° C. within 5 minutes with a solution of 6.4 g of 3-[trans-4-(p-cyanophenyl)cyclohexyl]propionaldehyde in 40 ml of t-butyl methyl ether and stirred at room temperature for a further 15 hours. The mixture was subsequently partitioned three times in diethyl ether/water. The organic extracts were washed twice with water, dried over magnesium sulphate, filtered and concentrated. In order to separate triphenylphosphine oxide, the residue was dissolved in ethyl acetate and the solution was diluted with petroleum ether, filtered and concentrated. Chromatographic separation of the resulting, yellowish oil (8.55 g) on silica gel with ethyl acetate/petroleum ether (vol. 3:97) gave 5.93 g (89%) of p-[trans-4-(3-pentenyl)cyclohexyl]benzonitrile as white crystals.

(b) A solution of 4.49 g of 90% m-chloroperbenzoic acid in 100 ml of methylene chloride was treated with 11.3 g of powdered potassium carbonate. The mixture was treated dropwise at 0° C. within 5 minutes with a solution of 5.93 g of p-[trans-4-(3-pentenyl)cyclohexyl]benzonitrile in 20 ml of methylene chloride and stirred at room temperature for 2 hours. The mixture was subsequently treated with a further 4.49 g of 90% m-chloroperbenzoic acid and the resulting mixture was stirred further. After a total of 70 hours, the mixture was partitioned three times in methylene chloride/10% sodium thiosulphate solution. The organic extracts were washed with sodium thiosulphate solution and water, dried over magnesium sulphate, filtered and concentrated. Chromatographic separation of the resulting, light yellowish oil (6.3 g) on silica gel with ethyl acetate/petroleum ether (vol. 10:90) gave 6.27 g (99.5%) of p-[trans-4-(3,4-epoxypentyl)cyclohexyl]benzonitrile as a colourless oil.

(c) A solution of 7.4 g of triphenylphosphine in 80 ml of methylene chloride was treated dropwise with a solution of 1.5 ml of bromine in 20 ml of methylene chloride while gassing with argon until the yellow colour remained. The mixture was then evaporated on a rotary evaporator and the residue was dried in a high vacuum for 1 hour. The yellow, crystalline residue was suspended in 120 ml of benzene. The suspension was treated with 6.27 g of p-[trans-4-(3,4-epoxypentyl)cyclohexyl]benzonitrile and heated to reflux while stirring for 1 hour. The mixture was subsequently filtered on silica gel using toluene as the eluent. Concentration of the product-containing fractions finally gave 9.54 g (99.1%) of p-[trans-4-(erythro-3,4-dibromopentyl)cyclohexyl]benzonitrile as a light brownish oil.

EXAMPLE 14

A solution of methylmagnesium iodide in diethyl ether (prepared from 384 mg of magnesium shavings and 0.984 ml of methyl iodide in 30 ml of diethyl ether) was treated dropwise at room temperature with a solution of 2.0 g of p-[trans-4-(trans-1-pentenyl)cyclohexyl]benzonitrile. The mixture was heated to reflux for 15 minutes. 30 ml of toluene were subsequently added to the mixture, the diethyl ether was distilled off and the resulting mixture was heated to reflux for a further 1.5 hours. The mixture was then treated cautiously at 0° C. with saturated ammonium chloride solution and partitioned three times in diethyl ether/water. The organic extracts were washed twice with water, dried over magnesium sulphate, filtered and evaporated. Chromatographic separation of the yellow, crystalline residue (2.6 g) on silica gel with ethyl acetate/petroleum ether (vol. 5:95) gave 1.85 g (87%) of p-[trans-4-(trans-1-pentenyl)cyclohexyl]acetophenone as light yellow crystals.

EXAMPLE 15

A solution of 1.35 g of p-[trans-4-(trans-1-pentenyl)cyclohexyl]acetophenone in 16 ml of ethanol and 16 ml of diethylene glycol was treated with 0.486 ml of hydrazine hydrate while gassing with argon and then heated to reflux (bath temperature 110° C.) while stirring for 1.5 hours. The mixture was subsequently treated with 550 mg of solid potassium hydroxide, the bath temperature was increased to 210° C. and the ethanol was distilled off. After 2.5 hours at 210° C., the reaction was interrupted and the mixture was partitioned three times in water/petroleum ether. The organic extracts were washed twice with water, dried over magnesium sulphate and evaporated. Chromatographic separation of the residue (1.23 g) on silica gel with hexane as the eluent gave 1.16 g (91%) of 4-ethyl-1-[trans-4-(trans-1-pentenyl)cyclohexyl]benzene as a colourless oil; m.p. (C-I) −3.1° C.

The following compounds were manufactured in an analogous manner:

4-Propyl-1-[trans-4-(trans-1-pentenyl)cyclohexyl]benzene; m.p. (C-I) 7.0° C., 4-ethyl-1-[2-(trans-4-(trans-1-propenyl)cyclohexyl)ethyl]benzene; m.p. (C-I) 1.7° C., cl.p. −26° C.

EXAMPLE 16

A suspension of 404.4 mg of diphosphorus tetraiodide in 5 ml of methylene chloride was treated dropwise while gassing with argon at room temperature within 5 minutes with a solution of 205 mg of 4-ethoxy-1-[trans-4-(1,2-epoxypentyl)cyclohexyl]benzene and 0.703 ml of pyridine in 8 ml of methylene chloride. The suspension was heated to reflux while stirring, a further 404.4 mg of diphosphorus tetraiodide being added after 2 hours. After stirring under reflux for a total of 19 hours, the reaction was interrupted and the mixture was treated with 1N hydrochloric acid and extracted three times with diethyl ether. The organic extracts were washed successively with 1N hydrochloric acid, sodium thiosulphate solution and water, dried over magnesium sulphate, filtered and evaporated. Chromatographic separation of the residue (0.2 g) on silica gel with ethyl acetate/petroleum ether (vol. 3:97) as the eluent gave 120 mg of 4-ethoxy-1-[trans-4-(trans-1-pentenyl)cyclohexyl]benzene. After recrystallization from 10 ml of methanol, the product was obtained as white crystals of melting point (C-N) 32.2° C. and clearing point (N-I) 54.9° C.

The 4-ethoxy-1-[trans-4-(1,2-epoxypentyl)cyclohexyl]benzene used as the starting material was prepared as follows:

(a) A solution of 2.63 g of p-[trans-4-(trans-1-pentenyl)cyclohexyl]acetophenone in 90 ml of methylene chloride was treated successively with 7.46 g of m-chloroperbenzoic acid and 100 mg of 2,6-di(t-butyl)-p-cresol at 0° C. while gassing with argon. The mixture was stirred at room temperature for 40 hours with the exclusion of light. The mixture was subsequently partitioned in methylene chloride/10% sodium thiosulphate solution and the organic phase was washed once with 10% sodium thiosulphate solution and twice with sodium hydrogen carbonate solution. The aqueous phases were backextracted three times with methylene chloride. The combined organic phases were dried over magnesium sulphate, filtered and evaporated. The yellow, oily residue of 4-acetoxy-1-[trans-4-(1,2-epoxypentyl)cyclohexyl]benzene was dissolved in 100 ml of 1N methanolic potassium hydroxide solution and stirred at room temperature for 1 hour. The mixture was subsequently adjusted to about pH 8 with 10 ml of 25% hydrochloric acid and partitioned in diethyl ether/water. The aqueous phase was extracted three times with diethyl ether. The organic phases were dried over magnesium sulphate, filtered and evaporated. Chromatographic separation of the resulting, brown oil (2.96 g) on silica gel with ethyl acetate/petroleum ether (vol. 10:90) gave 2.16 g of p-[trans-4-(1,2-epoxypentyl)cyclohexyl]phenol as yellowish crystals.

(b) A solution of 1.6 g of p-[trans-4-(1,2-epoxypentyl)cyclohexyl]phenol in 120 ml of acetone was treated with 1.89 ml of ethyl iodide and 3.24 g of powdered potassium carbonate while gassing with argon. The mixture was heated to reflux while stirring for 24 hours, then evaporated on a rotary evaporator and the residue was partitioned in diethyl ether/water. The aqueous phase was extracted three times with diethyl ether. The organic phases were washed twice with water, dried over magnesium sulphate, filtered and evaporated. Chromatographic separation of the resulting, yellowish oil (1.76 g) on silica gel with ethyl acetate/petroleum ether (vol. 5:95) gave 1.45 g (82%) of 4-ethoxy-1-[trans-4-(1,2-epoxypentyl)cyclohexyl]benzene as an oily liquid.

EXAMPLE 17

A mixture of 1.00 g of 2-(trans-1-pentenyl)-1,3-propanediol, 1.11 g of p-butoxybenzaldehyde, 3 drops of 2N sulphuric acid and 40 ml of toluene was heated to reflux for 2 hours with separation of water. The mixture was subsequently treated with 7 drops of triethylamine, left to cool, washed with 5 ml of saturated sodium hydrogen carbonate solution and three times with 10 ml of water each time, dried over sodium carbonate, filtered and concentrated. The semi-crystalline residue (1.86 g) was chromatographed on silica gel with hexane/diethyl ether (vol. 97:3). The product-containing fractions were pooled (0.99 g) and recrystallized twice from hexane at −25° C. There was obtained 0.44 g of pure trans-2-(p-butoxyphenyl)-5-(trans-1-pentenyl)m-dioxane; m.p. (C-N) 60.6° C., cl.p. (N-I) 61.9° C.

The 2-(trans-1-pentenyl)-1,3-propanediol used as the starting material was prepared as follows:

A solution of 16.1 g of diethyl 2-(trans-1-pentenyl)-malonate (Tetrahedron Lett. 1979, 861) in 75 ml of tetrahydrofuran was added dropwise to a suspension of 5.3 g of lithium aluminium hydride in 200 ml of dry tetrahydrofuran at 5° C. within 1 hour while stirring in an inert gas atmosphere. The mixture was stirred at room temperature for a further 3.5 hours and then successively treated dropwise with 15 ml of acetone and 20 ml of saturated sodium hydrogen carbonate solution. The mixture was filtered, the filtrate was concentrated and the residue (8.2 g) was distilled in a bulb-tube at 150° C./about 1 Torr. There were thus obtained 6.5 g of 2-(trans-1-pentenyl)-1,3-propanediol as a colourless oil.

The following compounds were manufactured in an analogous manner:

p-[Trans-5-(trans-1-propenyl)-m-dioxan-2-yl]benzonitrile; m.p. (C-I) 97° C., cl.p. (N-I) 73° C., p-[trans-5-(trans-1-butenyl)-m-dioxan-2-yl]benzonitrile; m.p. (C-I) 92.2° C., p-[trans-5-(trans-1-pentenyl)-m-dioxan-2-yl]benzonitrile; m.p. (C-I) 67.2° C., cl.p. (N-I) 59.1° C., p-[trans-5-(trans-1-hexenyl)-m-dioxan-2-yl]benzonitrile; m.p. (C-I) 50.5° C., cl.p. (N-I) 37.0° C., p-[trans-5-(trans-1-heptenyl)-m-dioxan-2-yl]benzonitrile; m.p. (C-I) 49.3° C., cl.p. (N-I) 49.2° C., trans-2-(p-ethoxyphenyl)-5-(trans-1-pentenyl)-m-dioxane; m.p. (C-I) 66.3° C., cl.p. (N-I) 64.4° C., trans-2-(p-ethoxyphenyl)-5-(trans-1-hexenyl)-m-dioxane; m.p. (C-I) 56.7° C., cl.p. (N-I) 47.5° C., trans-2-(p-butoxyphenyl)-5-(trans-1-propenyl)-m-dioxane; m.p. (C-N) 59.5° C., cl.p. (N-I) 61.2° C., trans-2-(p-butoxyphenyl)-5-(trans-1-hexenyl)-m-dioxane; m.p. (C-N) 30.5° C., $S_B$-N 30.3° C., cl.p. (N-I) 48.4° C., trans-2-(p-propylphenyl)-5-(trans-1-propenyl)-m-dioxane; m.p. (C-I) 57.8° C., trans-2-(p-propylphenyl)-5-(trans-1-pentenyl)-m-dioxane; m.p. (C-I) 45.2° C., cl.p. (S$_B$-I) 35.3° C.,
trans-2-(trans-4-butylcyclohexyl)-5-(trans-1-propenyl)-m-dioxane; m.p. (C-N) 47.3° C., cl.p. (N-I) 48.4° C.,
trans-2-(trans-4-propylcyclohexyl)-5-(trans-1-pentenyl)-m-dioxane; m.p. (C-S$_B$) 31.2° C., cl.p. (S$_B$-I) 85.7° C.

EXAMPLE 18

A mixture of 2.00 g of trans-4-cyanocyclohexanecarboxaldehyde, 2.13 g of 2-pentyl-1,3-propanediol and 65 mg of p-toluenesulphonic acid in 100 ml of benzene was heated to reflux for 3 hours while gassing with argon and with separation of water in a round flask provided with a water separator and a reflux condenser. The mixture was subsequently treated with 3.0 g of potassium carbonate, stirred at room temperature for 16 hours, then filtered and the filtrate was concentrated. Recrystallization of the crystalline residue (4.1 g) from hexane at 0° C. gave 1.47 g (38%) of trans-4-(trans-5-pentyl-m-dioxan-2-yl)cyclohexanecarbonitrile as colourless crystals in a purity of 99.1%. After a further recrystallization from hexane at 0° C., the purity increased to 99.9%; m.p. (C-N) 45.6° C., cl.p. (N-I) 46.7° C.

The following compounds were manufactured in an analogous manner:

Trans-4-(trans-5-propyl-m-dioxan-2-yl)cyclohexanecarbonitrile; m.p. (C-I) 63.6° C., cl.p. (N-I) 39.3° C.,
trans-4-(trans-5-butyl-m-dioxan-2-yl)cyclohexanecarbonitrile, m.p. (C-N) 33.2° C., cl.p. 35.6° C.,
trans-4-(trans-5-heptyl-m-dioxan-2-yl)cyclohexanecarbonitrile, m.p. (C-I) 56.3° C., cl.p. (N-I) 45.0° C.

I claim:

1. A compound of the formula:

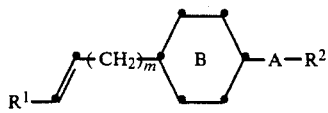

wherein $R^1$ is hydrogen or straight-chain alkyl; $R^2$ is —CN, —R, —COR, —COOR or when $R^2$ is positioned on an aromatic ring $R^2$ also can be —OR or —OOCR; R is alkyl; A is a group with 1 to 4 six-membered rings, these rings being linked directly with one another and with ring B in each case via a single covalent bond or being linked at one or two positions also via —COO—, —OOC— or —CH$_2$—CH$_2$—; ring B is trans-1,4-cyclohexylene and the six-membered rings in A each are 1,4-phenylene or trans-1,4-cyclohexylene or one of these rings in A also is trans-2,5-disubstituted m-dioxane, 2,5-disubstituted pyrimidine or 3,6-disubstituted pyridazine; or ring B is trans-2,5-disubstituted m-dioxane and the six membered rings in A each are 1,4-phenylene or trans-1,4-cyclohexylene; with the proviso that a maximum of two adjacent trans-1,4-cyclohexylene rings are linked directly via a single covalent bond and with the further proviso that ring B or one of the rings in group A is a heterocyclic ring when ring B and group A are linked directly via a single covalent bond; and m is the integer 0 or 2.

2. The compound of the claim 1, wherein the compound has the formula:

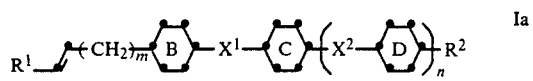

wherein ring B is trans-1,4-cyclohexylene or trans-2,5-disubstituted m-dioxane; rings C and D each are 1,4-phenylene, trans-1,4-cyclohexylene or when ring B is trans-1,4-cyclohexylene one of rings C and D also can be trans-2,5-disubstituted m-dioxane, 2,5-disubstituted pyrimidine or 3,6-disubstituted pyridazine; $X^2$ is a single covalent bond and $X^1$ is —COO—, —OOC—, —CH$_2$—CH$_2$—, or when one of the rings B, C and D is a heterocyclic ring and $X^1$ is a single covalent bond $X^2$ also can be a single covalent bond, —COO—, —OOC— or —CH$_2$—CH$_2$; n is the integer 0 or 1; and $R^1$, $R^2$, R and m have the significances given in claim 1.

3. The compound of claim 2, wherein n is the integer 0.

4. The compound of claim 1, wherein the compound has the formula:

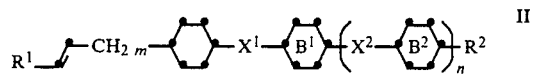

wherein each of rings $B^1$ and $B^2$ is 1,4-phenylene or trans-1,4-cyclohexylene; $X^2$ is a single covalent bond and $X^1$ is —COO—, —OOC—, or —CH$_2$—CH$_2$—; n is the integer 0 or 1; and $R^1$, $R^2$, R and m have the significances given in claim 1.

5. The compound of claim 4, wherein $X^1$ is —COO—, —OOC—, or —CH$_2$—CH$_2$—; $X^2$ is a single covalent bond; and each of rings $B^1$ and $B^2$ is 1,4-phenylene.

6. The compound of claim 1, wherein the compound has the formula:

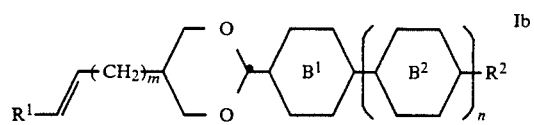

wherein each of rings $B^1$ and $B^2$ is 1,4-phenylene or trans-1,4-cyclohexylene; n is the integer 0 or 1; and $R^1$, $R^2$, R and m have the significances given in claim 1.

7. The compound of claim 6, wherein ring $B^1$ is 1,4-phenylene.

8. The compound of claim 1, wherein the compound has the formula:

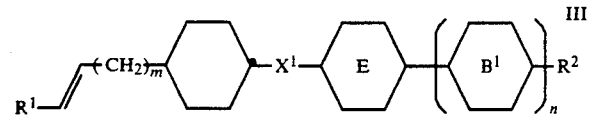

wherein ring E is 2,5-disubstituted pyrimidine; ring $B^1$ is 1,4-phenylene or trans-1,4-cyclohexylene; $X^1$ is a single covalent bond, —COO—, —OOC— or —CH$_2$CH$_2$—; n is the integer 0 or 1; and $R^1$, $R^2$, R and m have the significances given in claim 1.

9. The compound of claim 8, wherein $X^1$ is located at the 5-position of the pyrimidine ring and $X^1$ is a single covalent bond.

10. The compound of claim 1, wherein $R^1$ is straight-chain $C_1$-$C_{12}$-alkyl.

11. The compound of claim 1, wherein $R^2$ is cyano, alkyl, or when $R^2$ is positioned on an aromatic ring $R^2$ also can be alkoxy.

12. The compound of claim 11, wherein $R^2$ is cyano, $C_3$-$C_7$-alkyl, or when $R^2$ is positioned on an aromatic ring $R^2$ also can be $C_2$-$C_6$-alkoxy.

13. The compound of claim 1, wherein $R^1$ is hydrogen or straight-chain $C_1$-$C_{10}$-alkyl, and m is the integer 0.

14. The compound of claim 12, wherein $R^1$ is hydrogen or straight-chain $C_1$-$C_5$-alkyl, and m is the integer 0.

15. The compound of claim 1, wherein $R^1$ is hydrogen or straight-chain $C_1$-$C_8$-alkyl, and m is the integer 2.

16. The compound of claim 15, wherein $R^1$ is hydrogen or straight-chain $C_1$-$C_3$-alkyl, and m is the integer 2.

17. The compound of claim 1, wherein the compound has the formula:

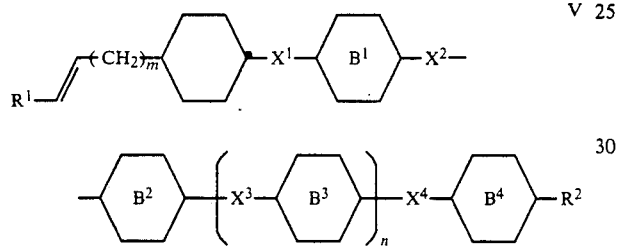

V wherein each of rings $B^1$, $B^2$, $B^3$ and $B^4$ is 1,4-phenylene or trans-1,4-cyclohexylene; n is the integer 0 or 1; $X^1$ is —COO—, —OOC—, or —CH$_2$—CH$_2$—; each of, $X^2$, $X^3$ and $X^4$ is a single covalent bond or one of these symbols also is —COO—, —OOC—, or —CH$_2$—CH$_2$—, with the proviso that a maximum of two adjacent trans-1,4-cyclohexylene rings are linked directly via a single covalent bond; and $R^1$, $R^2$, R and m have the significances give in claim 1.

18. The compound of claim 17, wherein m is the integer 0.

19. The compound of claim 1, wherein the compound has the formula:

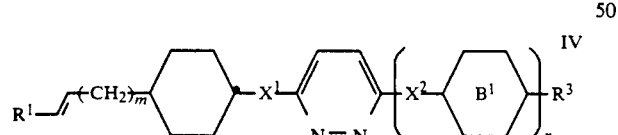

IV wherein ring $B^1$ is 1,4-phenylene or trans-1,4-cyclohexylene; each of $X^1$ and $X^2$ is a single covalent bond or one of $X^1$ and $X^2$ also is —COO—, —OOC— or —CH$_2$CH$_2$—; n is the integer 0 or 1; $R^3$ is —R, —COR, —COOR, or when $R^3$ is positioned on an aromatic ring $R^3$ also can be —OR or —OOCR; and $R^1$, R and m have the significances given in claim 1.

20. The compound of claim 1, p-[2-(trans-4-(trans-1-propenyl)cyclohexyl)ethyl]benzonitrile.

21. The compound of claim 1, p-[trans-5-(trans-1-propenyl)-m-dioxan-2-yl]benzonitrile.

22. The compound of claim 1, p-[trans-5-(trans-1-butenyl)-m-dioxan-2-yl]benzonitrile.

23. The compound of claim 1, p-[trans-5-(trans-1-pentenyl)-m-dioxan-2-yl]benzonitrile.

24. A liquid crystalline mixture comprising at least two components, wherein at least one component is a compound of the formula:

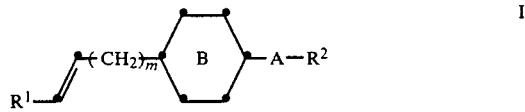

I wherein $R^1$ is hydrogen or straight-chain alkyl; $R^2$ is —CN, —R, —COR, —COOR or when $R^2$ is positioned on an aromatic ring $R^2$ also can be —OR or —OOCR; R is alkyl; A is a group with 1 to 4 six-membered rings, these rings being linked directly with one another and with ring B in each case via a single covalent bond or being linked at one or two positions also via —COO—, —OOC— or —CH$_2$—CH$_2$—; ring B is trans-1,4-cyclohexylene and the six-membered rings in A each are 1,4-phenylene or trans-1,4-cyclohexylene or one of these rings in A also is trans-2,5-disubstituted m-dioxane, 2,5-disubstituted pyrimidine or 3,6-disubstituted pyridazine; or ring B is trans-2,5-disubstituted m-dioxane and the six membered rings in A each are 1,4-phenylene or trans-1,4-cyclohexylene; with the proviso that a maximum of two adjacent trans-1,4-cyclohexylene rings are linked directly via a single covalent bond and with the further proviso that ring B or one of the rings in group A is a heterocyclic ring when ring B and group A are linked directly via a single covalent bond; and m is the integer 0 or 2.

25. The liquid crystalline mixture of claim 24, wherein the other component is one or more compounds selected from the group consisting of:

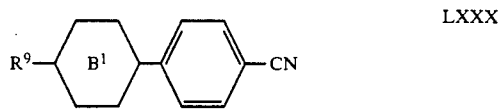

LXXX

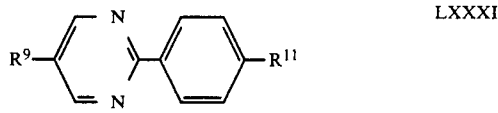

LXXXI

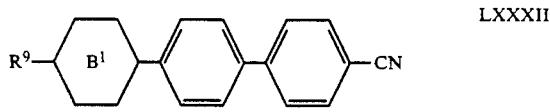

LXXXII

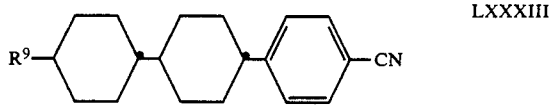

LXXXIII

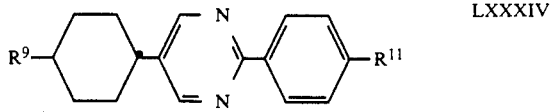

LXXXIV

-continued

LXXXV
R⁹—[B¹]—COO—[phenyl]—R¹⁰

LXXXVI
R⁹—[cyclohexyl]—COO—[cyclohexyl]—R¹²

LXXXVII
R¹²—[phenyl]—N=N(O)—[phenyl]—R¹³

LXXXVIII
R⁹—[cyclohexyl]—CH₂CH₂—[phenyl]—([phenyl])ₚ—R¹¹

LXXXIX
R¹²—[cyclohexyl]—[phenyl]—([phenyl])ₚ—[cyclohexyl]—R¹³

XC
R¹⁴—[phenyl]—CH₂CH₂—R¹⁵;

and

XCI
R¹⁶—[B¹]—Z¹—[B²]—Z²—

—[B³]—Z³—([B⁴]—Z⁴)ₚ—[B⁵]—R¹⁷ wherein ring B¹ is 1,4-phenylene or trans-1,4-cyclohexylene; R⁹ is straight-chain $C_2$-$C_7$-alkyl; R¹⁰ is cyano or straight-chain $C_1$-$C_6$-alkoxy, R¹¹ is cyano, straight-chain $C_1$-$C_7$-alkyl or $C_1$-$C_7$-alkoxy; each of R¹² and R¹³ is straight-chain $C_1$-$C_7$-alkyl; p is the integer 0 or 1; R¹⁴ is trans-4-alkylcyclohexyl, 4′-alkyl-4-biphenylyl, p-(trans-4-alkylcyclohexyl)phenyl, 2-(trans-4-alkylcyclohexyl)ethyl or p-[2-(trans-4-alkylcyclohexyl)ethyl]phenyl and R¹⁵ is trans-4-alkylcyclohexyl; or R¹⁴ is trans-4-alkylcyclohexyl and R¹⁵ is p-(trans-4-alkylcyclohexyl)phenyl, p-[2-(trans-4-alkylcyclohexyl)ethyl]phenyl or 4′-(trans-4-alkyl-cyclohexyl)-4-biphenylyl; or R¹⁴ is p-alkylphenyl and R¹⁵ is p-[2-(trans-4-alkylcyclohexyl)ethyl]phenyl; each of the alkyl groups in R¹⁴ and R¹⁵ is straight-chain $C_1$-$C_7$-alkyl; one of Z¹ and Z² is —COO— or —OOC— and the other as well as each of Z³ and Z⁴ are single covalent bonds or one of Z¹, Z², Z³ and Z⁴ also can be —CH₂CH₂—; each of rings B¹ and B⁵ in formula XCI is a group of the formula XCII
[phenyl with Y substituent]

or trans-1,4-cyclohexylene; each of rings B², B³ and B⁴ is a group of formula XCII, or when rings B², B³ and B⁴ are not linked with at least one of the other two of these rings by a single covalent bond, rings B², B³ and B⁴ also can be trans-1,4-cyclohexylene; Y is hydrogen or when Y is positioned on one of the rings of formula XCII which is not linked with a further ring via a single covalent bond, Y also can be fluorine, chlorine or methyl; each of R¹⁶ and R¹⁷ is straight-chain $C_1$-$C_7$-alkyl or when positioned on a ring of formula XCII R¹⁶ and R¹⁷ also can be straight-chain $C_1$-$C_7$-alkoxy.

26. The liquid crystalline mixture of claim 24, wherein the other component is a compound of the formula:

LXXVIII
R⁸—[dioxane]—[cyclohexyl]—CN wherein R⁸ is straight-chain $C_1$-$C_{12}$ alkyl.

27. An electro-optical cell comprising:
(a) two plate means;
(b) liquid crystal means disposed between the two plate means and including a compound of the formula;

I
R¹—[CH=CH—(CH₂)ₘ]—[B]—A—R² wherein R¹ is hydrogen or straight-chain alkyl; R² is —CN, —R, —COR, —COOR or when R² is positioned on an aromatic ring R² also can be —OR or —OOCR; R is alkyl; A is a group with 1 to 4 six-membered rings, these rings being linked directly with one another and with ring B in each case via a single covalent bond or being linked at one or two positions also via —COO—, —OOC— or —CH₂—CH₂—; ring B is trans-1,4-cyclohexylene and the six-membered rings in A each are 1,4-phenylene or trans-1,4-cyclohexylene or one of these rings in A also is trans-2,5-disubstituted m-dioxane, 2,5-disubstituted pyrimidine or 3,6-disubstituted pyridazine; or ring B is trans-2,5-disubstituted m-dioxane and the six membered rings in A each are 1,4-phenylene or trans-1,4-cyclohexylene; with the proviso that a maximum of two adjacent trans-1,4-cyclohexylene rings are linked directly via a single covalent bond and with the further proviso that ring B or one of the rings in group A is a heterocyclic ring when ring B and group A are linked directly via a single covalent bond; and m is the integer 0 or 2; and
(c) means for applying an electrical potential to said plate means.

* * * * *